(12) United States Patent
Hartung et al.

(10) Patent No.: US 8,955,969 B2
(45) Date of Patent: Feb. 17, 2015

(54) OCULAR IMAGING

(75) Inventors: Paul D. Hartung, Acton, MA (US); Vincent Valvo, Southborough, MA (US); Dennis J. Nilan, Milford, MA (US)

(73) Assignee: Cognoptix, Inc., Acton, MA (US)

( * ) Notice: Subject to any disclaimer, the term of this patent is extended or adjusted under 35 U.S.C. 154(b) by 551 days.

(21) Appl. No.: 12/933,591

(22) PCT Filed: Mar. 27, 2009

(86) PCT No.: PCT/US2009/001885
§ 371 (c)(1), (2), (4) Date: Jan. 4, 2011

(87) PCT Pub. No.: WO2009/120349
PCT Pub. Date: Oct. 1, 2009

(65) Prior Publication Data
US 2011/0116041 A1 May 19, 2011

Related U.S. Application Data

(63) Continuation-in-part of application No. 11/786,514, filed on Apr. 11, 2007, now Pat. No. 7,828,436.

(60) Provisional application No. 61/072,199, filed on Mar. 27, 2008, provisional application No. 60/791,288, filed on Apr. 11, 2006.

(51) Int. Cl.
*A61B 3/10* (2006.01)
*A61B 3/117* (2006.01)

(52) U.S. Cl.
CPC .. *A61B 3/117* (2013.01); *A61B 3/10* (2013.01)
USPC ............................. 351/206; 351/246; 351/221

(58) Field of Classification Search
CPC .................................. A61B 3/117; A61B 3/10
USPC .................................. 351/206, 213, 221, 246
See application file for complete search history.

(56) References Cited

U.S. PATENT DOCUMENTS 4,209,225 A 6/1980 Abe et al.
4,529,556 A 7/1985 Bruza
(Continued)

FOREIGN PATENT DOCUMENTS

DE 10 2007 061 987 A1 6/2009
EP 0 628 281 A1 6/1994
(Continued)

OTHER PUBLICATIONS

Hartung, P., "Optical Biosensors: Lasers Look Alzheizer's in the Eye," Laser Focus World vol. 42, No. 10 [online], Oct. 1, 2006 [retrieved on Oct. 26, 2011]. Retrieved from the Internet URL: http://www.laserfocusworld.com.
(Continued)

*Primary Examiner* — Zachary Wilkes
(74) *Attorney, Agent, or Firm* — Hamilton, Brook, Smith & Reynolds, P.C.

(57) ABSTRACT

A system for performing at least one of quasi-elastic light scattering and fluorescent ligand scanning on a subject's eye includes a light source configured to transmit light toward the subject's eye, a lens configured to focus light sent from the source and received from the subject's eye, a measurement reflector disposed to receive at least a portion of the focused light and configured to reflect a first portion of the received light, a camera configured and disposed to receive the first portion of the received light and configured to provide indicia of an image corresponding to the first portion of the received light, and a processor coupled to the camera and configured to analyze intensities of light in the image to determine a location of a reference point corresponding to an interface of a portion of the eye.

30 Claims, 12 Drawing Sheets

(56) References Cited

U.S. PATENT DOCUMENTS

| | | | |
|---|---|---|---|
| 4,702,576 A | 10/1987 | Magnante | |
| 4,761,071 A | 8/1988 | Baron | |
| 4,806,004 A | 2/1989 | Wayland | |
| 4,957,113 A | 9/1990 | Benedek | |
| 4,993,827 A | 2/1991 | Benedek et al. | |
| 5,013,146 A | 5/1991 | Akiyama | |
| 5,048,946 A | 9/1991 | Sklar et al. | |
| 5,183,044 A | 2/1993 | Nishio et al. | |
| 5,184,157 A | 2/1993 | Ichihashi et al. | |
| 5,400,091 A | 3/1995 | Okazaki | |
| 5,427,094 A * | 6/1995 | Thurston et al. | 600/318 |
| 5,540,226 A | 7/1996 | Thurston et al. | |
| 5,787,890 A | 8/1998 | Reiter et al. | |
| 5,864,382 A | 1/1999 | Soya et al. | |
| 5,880,813 A | 3/1999 | Thall | |
| 5,894,340 A | 4/1999 | Loree et al. | |
| 5,973,779 A | 10/1999 | Ansari et al. | |
| 6,045,503 A | 4/2000 | Grabner et al. | |
| 6,088,606 A | 7/2000 | Ignotz et al. | |
| 6,096,510 A | 8/2000 | Hochman | |
| 6,179,422 B1 | 1/2001 | Lai | |
| 6,229,907 B1 | 5/2001 | Okano et al. | |
| 6,280,386 B1 | 8/2001 | Alfano et al. | |
| 6,299,305 B1 * | 10/2001 | Miwa | 351/200 |
| 6,329,531 B1 | 12/2001 | Turner et al. | |
| 6,419,361 B2 * | 7/2002 | Cabib et al. | 351/221 |
| 6,478,424 B1 * | 11/2002 | Grinvald et al. | 351/206 |
| 6,605,081 B1 | 8/2003 | Shimmick et al. | |
| 7,147,328 B2 * | 12/2006 | Sugino et al. | 351/206 |
| 7,303,281 B2 | 12/2007 | Wakil et al. | |
| 7,452,078 B2 | 11/2008 | Isogai | |
| 7,828,436 B2 | 11/2010 | Goldstein et al. | |
| 8,388,134 B2 | 3/2013 | Goldstein et al. | |
| 8,439,501 B2 | 5/2013 | Newman et al. | |
| 2002/0091321 A1 | 7/2002 | Goldstein et al. | |
| 2003/0090626 A1 | 5/2003 | Lai et al. | |
| 2004/0116811 A1 | 6/2004 | Koschmieder | |
| 2004/0152068 A1 | 8/2004 | Goldstein et al. | |
| 2004/0254154 A1 | 12/2004 | Ashton | |
| 2004/0267118 A1 | 12/2004 | Dawson | |
| 2007/0171366 A1 | 7/2007 | Su et al. | |
| 2011/0080559 A1 | 4/2011 | Goldstein et al. | |
| 2013/0114042 A1 | 5/2013 | Goldstein et al. | |
| 2013/0135580 A1 | 5/2013 | Hartung et al. | |

FOREIGN PATENT DOCUMENTS

| | | |
|---|---|---|
| EP | 0 983 757 A2 | 9/1999 |
| EP | 1913866 A1 | 4/2008 |
| EP | 2 268 193 | 1/2011 |
| EP | 2420179 A2 | 2/2012 |
| GB | 2 407 378 A | 4/2005 |
| GB | 2 409 033 A | 6/2005 |
| JP | 09-218155 | 8/1997 |
| WO | WO 92/11799 | 7/1992 |
| WO | WO 94/06346 | 5/1994 |
| WO | WO 95/00068 | 1/1995 |
| WO | WO 95/13010 | 5/1995 |
| WO | WO 95/13011 | 5/1995 |
| WO | WO 99/18868 | 4/1999 |
| WO | WO 00/56204 | 9/2000 |
| WO | WO 02/16951 A2 | 2/2002 |
| WO | WO 02/064031 A2 | 8/2002 |
| WO | WO 03/018068 A1 | 3/2003 |
| WO | WO 03/032823 A2 | 4/2003 |
| WO | WO 03/090613 A1 | 11/2003 |
| WO | WO 2004/034894 A1 | 4/2004 |
| WO | WO 2007/120755 A2 | 10/2007 |
| WO | WO 2008/000403 A2 | 1/2008 |
| WO | WO 2008/144065 A1 | 11/2008 |
| WO | WO 2009/120349 A1 | 10/2009 |
| WO | WO 2010-097582 A1 | 9/2010 |

OTHER PUBLICATIONS

Patent Tanslate: Machine Translation to English for Description DE102007061987, consisting of 9 pages, dated Jul. 30, 2012.

Apr. 25, 2012, Office Action, U.S. Appl. No. 12/897,432.

Nov. 11, 2011, Invitation to Pay Additional Fees and, Where Applicable, Protest Fee, PCT/US2011/047628.

Jan. 31, 2012, Notification of Transmittal of the International Scarch Report and the Written Opinion of the International Searching Authority, or the Declaration, PCT/US2011/047628.

Ansari, R.R., et al., "Measuring Lens Opacity: Combining Quasi-Elastic Light Scattering with Scheimpflug Imaging System," *Proceedings of SPIE*, 3246: 35-42 (1999).

Ansari, R.R. and Datiles, III, M. B. "Use of Dynamic Light Scattering and Scheimpflug Imaging for the Early Detection of Cataracts," *Diabetes Technology & Therapeutics*, 1(2): 159-169 (1999).

Chylack, L.T., et al., "Optiscan 2400, a New Clinical Instrument for Non-Invasive Measurement of Quasi-Elastic Light Scattering in Human Lens In Vivo," *Invest Opthalmol Vis Sci*, 46, E-Abstract 2911 (2002).

Dhenain, M., "Preclinical NRI and NMR Biomarkers of Alzheimer's Disease: Concepts and Applications," *Magnetic Resonance Insights*, 2: 75-91 (2008).

Goldstein, L.E., et al., "Cytosolic β-amyloid Deposition and Supranuclear Cataracts in Lenses from People with Alzheimer's Disease," *The Lancet*, 361: 1258-1265 (2003).

Jones-Bey, H., "Optical Technique May Diagnose Alzheimer's," *Laser Focus World*, 41(11) 2 pages (2005).

Apr. 15, 2009, Restriction Requirement, U.S. Appl. No. 11/786,514.

Jun. 15, 2009, Reply to Restriction Requirement, U.S. Appl. No. 11/786,514.

Sep. 30, 2009, Office Action, U.S. Appl. No. 11/786,514.

Feb. 26, 2010, Amendment filed, U.S. Appl. No. 11/786,514.

Jul. 8, 2010, Notice of Allowance, U.S. Appl. No. 11/786,514.

Oct. 5, 2010, Issue Fee Paid, U.S. Appl. No. 11/786,514.

Nov. 9, 2010, Issue Notification, U.S. Appl. No. 11/786,514.

Mar. 26, 2008, Communication from European Patent Office containing extended European Search Report, 07023740.9.

May 6, 2008, Invitation to Pay Additional Fees, PCT/US2007/009009.

Jul. 9, 2008, Notification of Transmittal of the International Search Report and the Written Opinion, PCT/US2007/009009.

Oct. 11, 2008, Written Opinion of the International Searching Authority, PCT/US2007/009009.

Oct. 23, 2008, Notification Concerning Transmittal of International Preliminary Report on Patentability, PCT/US2007/009009.

Nov. 26, 2008, Communication from European Patent Office regarding invitation to file observations, 07023740.9.

Mar. 31, 2009, Response to Invitation to file observations, 07023740.9.

May 26, 2009, Communication pursuant to Article 94(3) EPC, 07 755 321.2.

Jun. 26, 2009, Notification of Transmittal of the International Search Report and the written Opinion of the International Search Authority, PCT/US2009/001885.

Jul. 24, 2009, Summons to Attend Oral Proceedings pursuant to Rule 115(1) EPC, 07023740.9.

Sep. 18, 2009, Result of Consultation, 07023740.9.

Sep. 30, 2009, Response to Summons to Attend Oral Proceedings pursuant to Rule 115(1) EPC, 07023740.9.

Oct. 8, 2009, Result of Consultation, 07023740.9.

Oct. 26, 2009, 4th and 5th Auxiliary request filed for reconsideration, 07023740.9.

Nov. 10, 2009, Result of Consultation, 07023740.9.

Nov. 26, 2009, Decision to Refuse a European Patent Application, 07023740.9.

Mar. 15, 2010, Response to Communication pursuant to Article 94(3) EPC dated May 26, 2009. 07755321.2.

Mar. 26, 2010, Statement of Grounds of the Appeal, 07023740.9.

Apr. 6, 2010, Request for Examination and Voluntary Amendment. 2009-505473.

Jul. 6, 2010, Direction to Request for Examination from Commissioner of Patents. 2007238693.

(56) References Cited

OTHER PUBLICATIONS

Sep. 27, 2010, Written Opinion of the International Searching Authority, PCT/US2009/001885.
Sep. 28, 2010, International Preliminary Report on Patentability, PCT/US2009/001885.
Sep. 30, 2010, Request for Examination. 2007238693.
Oct. 7, 2010, Notification Concerning the Transmittal of International Preliminary Report on Patentability. PCT/US2009/001885.
Nov. 8, 2010, Communication pursuant to Rules 161(1) and 162 EPC. 09723695.4.
Dec. 8, 2010, Communication of European publication. 09723695.4.
Dec. 20, 2010, Reply to Communication pursuant to Rules 161(1) and 162 EPC, 09723695.4.
May 4, 2011, Notice of Publication, 200980113126.7.
Notice of Allowance for U.S. Appl. No. 12/897,432 dated Oct. 4, 2012.
"Notification Concerning Transmittal of International Preliminary Report on Patentability (Chapter I of the Patent Cooperation Treaty)" from International Application No. PCT/US2011/047628 mailed on Feb. 28, 2013.
Office Action dated Aug. 29, 2013 for U.S. Appl. No. 13/732,940, filed Jan. 2, 2013 entitled "Ocular Imaging".
Notification of Transmittal of the International Search Report and the Written Opinion of the International Searching Authority, or the Declaration, International Application No. PCT/US2013/069598, mailed Jul. 31, 2014, "Method for Measuring Fluorescence in Ocular Tissue".

* cited by examiner

OCULAR IMAGING

CROSS-REFERENCE TO RELATED APPLICATIONS

This application is the U.S. National Stage of International Application No. PCT/US2009/001885, filed Mar. 27, 2009, which designates the U.S., published in English, and claims the benefit of U.S. Provisional Application No. 61/072,199, filed Mar. 27, 2008. This application is a Continuation-in-Part of U.S. application Ser. No. 11/786,514, filed on Apr. 11, 2007 now U.S. Pat. No. 7,828,436, which claims priority to U.S. Provisional No. 60/791,288, filed Apr. 11, 2006. The entire teachings of the above applications are incorporated herein by reference. The entire disclosure of U.S. Pat. No. 7,107,092 is also incorporated herein by reference.

BACKGROUND

It is always desirable to detect diseases early in their progress. Early detection enables early treatment which has generally been proven to yield a higher success rate in treating various diseases. Recently, it has been discovered that analyzing peoples' eyes, and in particular the lenses of the eyes, can yield indications of various types of diseases. For example, measurements taken of light scattering within the eye has been shown to provide useful diagnostic information to detect and monitor the progress of diseases such as Alzheimer Disease [AD]. This disease in particular has recently been shown to cause changes in the supra-nuclear region of the lens of the eye. Since this region is only a fraction of a millimeter thick, measurements of this region, to be useful, need to be very accurate in the information for the position of the measurement. This is especially true because the human eye is in almost constant motion even when a patient is fixating on an illuminated target.

It has been shown that the presence of or an increase in the amount of aggregate in the supranuclear and/or cortical lens regions of a test mammal's eye compared to a normal control value indicates that the test mammal is suffering from, or is at risk of, developing a neurodegenerative disease such as an amyloidogenic disorder. Amyloidogenic disorders include AD, Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegeneration with brain iron accumulation (Hallervorden-Spatz Disease), synucleinopathies (including Parkinson's disease, multiple system atrophy, dementia with Lewy Bodies, and others), neuronal intranuclear inclusion disease, tauopathies (including progressive supranuclear palsy, Pick's disease, corticobasal degeneration, hereditary frontotemporal dementia (with or without Parkinsonism), and Guam amyotrophic lateral sclerosis/parkinsonism dementia complex). These disorders may occur alone or in various combinations. Aggregate analysis is also useful to detect Transmissible Spongiform Encephalopathies (TSEs), which are prion-mediated diseases characterized by fatal spongiform neurodegeneration of the brain and are associated with severe and fatal neurological signs and symptoms. TSE prionopathies include Creutzfeld-Jacob Disease (CJD); new variant, Creutzfeld-Jacob Disease (nv-CJD); Gertsmann-Straussler-Scheinker syndrome; fatal familial insomnia; Kuru; Alpers Syndrome; Bovine Spongiform Encephalopathy (BSE); scrapie; and chronic wasting disease (CWD).

SUMMARY

In general, in some aspects, the invention provides a system for performing quasi-elastic light scattering and fluorescent ligand scanning on a subject's eye. The system may include a light source configured to transmit light toward the subject's eye, a lens configured to focus light sent from the source and scattered by the subject's eye, a measurement reflector disposed to receive at least a portion of the focused light and configured to reflect a first portion of the received light, a camera configured and disposed to receive the first portion of the received light and configured to provide indicia of an image corresponding to the first portion of the received light, and a processor coupled to the camera and configured to analyze intensities of light in the image to determine a location of a reference point corresponding to an interface of a portion of the eye.

The reference point may correspond to: an interface of a lens capsule of the eye; an interface between the lens capsule and an anterior chamber of the eye; one of a posterior lens capsule interface; an air-cornea interface; a cornea-aqueous interface, and an interface of a retina of the eye. Moreover, the light source and processor may be configured to perform fluorescent ligand scanning. To that end, the system may be configured such that light scattered only at substantially 90° relative to a path of the light entering the subject's eye is collected and analyzed.

Further, implementations of the invention may also include one or more of the following features:
A light source configured to transmit infrared light.
A measurement reflector including a mirror configured to reflect the first portion of the received light, where the mirror defines an opening configured to allow a second portion of the received light to pass unreflected by the mirror.
A correlator coupled to the reflector to receive the second portion of the received light, which may be used to correlate measured scattered light intensity over time.
A processor configured to actuate the measurement reflector such that the second portion of the received light corresponds to light scattered from a selected portion of the eye relative to the reference point.
A processor coupled to the correlator and configured to analyze indicia of the second portion of the received light.
A processor configured to provide an indication of the presence of material associated with a medical condition of the subject based on the indicia of the second portion of the received light and a location in the eye from which the second portion of the received light was scattered.

Further, implementations of the invention may include one or more of the following features:
A processor configured to analyze light intensities in the image to determine locations of regions in the eye relative to the reference point.
A processor configured to associate the light intensities in the image with regions from which the light associated with the light intensities was scattered.
A processor configured to determine locations of a supranucleus, a nucleus, and a cortex of the eye.

The system, according to some embodiments, may further include a display coupled to the processor where the processor is configured to cause the processor to display an ellipse in the image and a light source configured to transmit a pencil beam and/or a fan beam of light. To that end, a processor may be configured to: adjust a size and position of the ellipse relative to the image; to analyze light intensities in the image to determine a location of an iris of the eye and to size and position the ellipse over the iris in the image; and/or configured to adjust the size of the ellipse in response to input from a user of the system.

In general, in another aspect, the invention provides a diagnostic light scattering method including transmitting a pencil beam of light into a subject's eye, acquiring light from the pencil beam scattered by the subject's eye, and analyzing the acquired scattered light to determine a location of a reference point corresponding to an interface of a portion of the eye.

The step of analyzing may include: determining the reference point as a point corresponding to an interface of a lens capsule of the eye; and evaluating intensity of light scattered by the eye to determine first and second regions of high intensity along a line of propagation of the pencil beam. To that end, the first and second regions may be separated by a relatively large third region substantially free of scattered light from the pencil beam, where the second region being further along the line of propagation from a source of the pencil beam and determined to correspond to the lens capsule. The analyzing may include determining the reference point as a point corresponding to one of an interface between the lens capsule and an anterior chamber of the eye, a posterior lens capsule interface, an air-cornea interface, a cornea-aqueous interface, and an interface of a retina of the eye. The analyzing may further include determining locations of a cortex, a supra-nucleus, and/or a nucleus of the eye.

Method aspects of the invention may further include analyzing intensity of light scattered from a selected portion of the eye relative to the reference point to determine a physical property of material at the selected portion, and providing an indication of the physical property of the material at the selected portion. The step of providing the indication may include providing an indication of presence of aggregates in a supra-nucleus of the eye.

The method aspects of the invention may further include forming an image from the acquired light, reflecting the pencil beam before the acquiring, determining an actual position of a particular portion of the acquired light in the image relative to a desired position of the particular portion of the acquired light, and altering the reflecting to reduce a separation of the actual position and the desired position of the particular portion of the acquired light.

The acquiring may include acquiring light scattered by the eye only at approximately 90° relative to a direction of propagation of the pencil beam.

Some method aspects of the invention may include transmitting of a fan beam of light into the subject's eye, acquiring light from the fan beam scattered by the subject's eye, forming an image of the eye from the acquired fan beam light scattered by the subject's eye, and superimposing an ellipse on the image approximating a size and location of an iris of the eye in the image. The superimposing may be done automatically by a computer, and may be formed by the computer through analysis by the computer of light intensities in the image.

Some method aspects include quasi-elastic light scattering and may be performed using a device. Such methods may further include performing fluorescent ligand scanning using the same device. The step of performing fluorescent ligand scanning may include illuminating the subject's eye, measuring first data of fluorescence of the eye before introducing an imaging agent into the eye, introducing the imaging agent into the eye, measuring second data of fluorescence of the eye after introducing the imaging agent into the eye, and comparing the first and second data.

In general, in another aspect, the invention provides a system for diagnostic imaging of a subject's eye the system includes a light source configured to transmit light by stimulated emission of radiation, an optical scanning device configured to produce a vertical fan beam of light from the light source and linearly sweep the vertical fan beam from side to side, a first lens configured to focus light sent from the optical scanning device to create an virtual image plane that is coplanar with a subject's line of sight and is a vertical cross-sectional plane through a portion of the subject's eye, a second lens configured to focus light sent from the optical scanning device and scattered by the subject's eye to create a sharp focus plane which coincides with the virtual image plane of the subject's eye, a first measurement reflector disposed to receive at least a portion of the focused light and configured to reflect a first portion of the received light, a first camera configured and disposed to receive the first portion of the received light and configured to provide indicia of an image corresponding to the first portion of the received light, and a processor coupled to the camera and configured to analyze intensities of light in the image to determine a location of a reference point corresponding to an interface of a portion of the eye wherein the linear sweep of the vertical fan beam from side to side by the optical scanning device traverses the vertical fan beam of light in and out along the virtual image plane of the subject's eye.

Implementations of the invention may include one or more of the following features. The reference point corresponds to an interface of a lens capsule of the eye. The reference point corresponds to an interface between the lens capsule and an anterior chamber of the eye. The reference point corresponds to one of a posterior lens capsule interface, an air-cornea interface, a cornea-aqueous interface, and an interface of a retina of the eye. The light source and processor are configured to perform fluorescent ligand scanning. The light source is configured to transmit infrared light. The system is configured such that light scattered only at substantially 90° relative to a path of the light entering the subject's eye is collected and analyzed.

Further, implementations of the invention may include one or more of the following features. The measurement reflector includes a mirror configured to reflect the first portion of the received light, the mirror defining an opening configured to allow a second portion of the received light to pass unreflected by the mirror, the system further comprising a correlator coupled to the reflector to receive the second portion of the received light and to correlate measured scattered light intensity over time. The processor is configured to actuate the measurement reflector such that the second portion of the received light corresponds to light scattered from a selected portion of the eye relative to the reference point, and wherein the processor is coupled to the correlator and configured to analyze indicia of the second portion of the received light. The processor is configured to provide an indication of the presence of material associated with a medical condition of the subject based on the indicia of the second portion of the received light and a location in the eye from which the second portion of the received light was scattered. The system further comprises a second measurement reflector disposed to receive at least a portion of the focused light and configured to reflect a second portion of the received light.

In general, in another aspect, the invention provides a system for performing at least one of quasi-elastic light scattering and fluorescent ligand scanning on a subject's eye, including a display screen showing an image of the eye to allow an operator to select locations in the eye to be measured. The system may include an optical unit coupled to a processor for executing at least one of quasi-elastic light scattering and fluorescent ligand scanning on selected locations of the eye and for collecting data associated with the quasi-elastic light scattering and/or fluorescent ligand scanning performed. The processor may further display data on the display screen for operator review. To that end, the data associated with the quasi-elastic light scattering and/or fluorescent ligand scanning may be reported on the same display screen and/or collected in cycles of no more than 60 msec. In some embodiments, the processor may execute up to ten consecutive cycles. Moreover, the data displayed on the display screen may include test settings, front and cross-sectional views of the eye, average intensity values of quasi-elastic light scattering and/or fluorescent ligand scanning, graphical depictions of autocorrelation functions for quasi-elastic light scattering and/or fluorescent ligand scanning, and curve fit parameters based on an exponential fit to the autocorrelation data. The data may be used to detect the presence of a material or object of interest, including without limitation, β-amyloid protein and/or track the progress of disease.

In some embodiments, the data collected by the system may include the average intensity of scattered light associated with quasi-elastic light scattering performed and/or the average fluorescence intensity associated with fluorescent ligand scanning performed. Implementations of the invention may collect data from locations in the nucleus and/or supranucleus regions of the lens of the eye to determine a ratio between the average fluorescence intensity associated with fluorescent ligand scanning of the nucleus region of the lens of the eye and the average fluorescence intensity of fluorescent ligand scanning of the supranucleus region of the lens of the eye. A similar ratio may be determined for quasi-elastic light scattering of the nucleus and supranucleus regions of the lens of the eye. The ratios may correlate to the state of a disease in the eye, such that an increase in a ratio indicates an increase in the amount of a material and/or object in the eye. Some embodiments may also incorporate a measurement quality metric calculated by multiplying these ratios together or using the curve, $y(t)=Ie-kt$, where I is the average intensity, k is the decay time constant and t is time.

Additional system aspects of the invention may include a display screen for displaying the image to allow an operator to select regions of the eye for analyzing, as well as a process configured to analyze scattered light from quasi-elastic light scattering and/or fluorescent emissions from fluorescent ligand scanning to detect a material or object of interest located in selected regions of the eye. The material or object of interest may be β-amyloid. In some embodiments, the average intensity of the scattered light and/or fluorescent emissions from a supranucleus and/or nucleus region of the lens of the eye may be analyzed. Moreover, the average intensity of scattered light or fluorescent emissions from the nucleus region of the lens of the eye may be compared to the average intensity of scattered light or fluorescence for the supranucleus region of the lens of the eye to provide a correlation factor for evaluating the presence of a material or object of interest in the eye. In some embodiments, the processor may measure the fluorescence intensity from a region of the eye before introduction of an imaging agent and after introduction of an imaging agent to determine the difference between the two intensities. In some embodiments, the processor may measure first data of fluorescence of the eye before introducing an imaging agent into the eye and second data of fluorescence of the eye after introducing the imaging agent and then compare the first data and the second data. The comparison may include, for example, subtracting the first data from the second data to determine a difference in measured fluorescence. Furthermore, the processor may display data from quasi-elastic light scattering and/or fluorescent ligand scanning on the display screen for operator review. The data may include any information on the quasi-elastic light scattering and/or fluorescent ligand scanning performed.

Another aspect of the invention provides a method of performing at least one of quasi-elastic light scattering and fluorescent ligand scanning to a subject's eye. The method may include selecting a location in the eye for collecting data, performing at least one of quasi-elastic light scattering and fluorescent ligand scanning on the selected location, collecting data from the quasi-elastic light scattering and/or fluorescent ligand scanning and presenting the data. The data may be displayed on a display screen and/or printed out. To that end, the data collected may include the average intensity of at least one of scattered light associated with quasi-elastic light scattering performed and average fluorescence intensity associated with fluorescent ligand scanning performed. The average intensity data may be collected from locations in the supranucleus and/or nucleus region of the lens of the eye and a ratio between the average intensity of scattered light from the nucleus region of the lens of the eye and the average intensity of scattered light from the supranucleus region of the lens of the eye may be determined. A similar ratio may be determined with respect to fluorescent ligand scanning.

Method aspects of the invention may further include performing fluorescent ligand scanning by illuminating the subject's eye, measuring first data of fluorescence of the eye before introducing an imaging agent into the eye, introducing the imaging agent into the eye, measuring second data of fluorescence of the eye after introducing the imaging agent into the eye and comparing the first data with the second data. In some embodiments, the first data and the second data may include the average fluorescence intensity from the eye and comparing the first data and the second data may include subtracting the first data from the second data. In some embodiments, the measurement of the second data may be taken no more than 24 hours after introducing the imaging agent into the eye. The method may also be capable of detecting the presence of β-amyloid protein in the eye and/or allowing the progress of a disease to be tracked by measuring levels of fluorescence in the eye.

Also, implementations of the invention may include one or more of the following features. The system further includes a second camera configured and disposed to receive the second portion of the received light and configured to provide indicia of an image corresponding to the second portion of the received light. The system further includes a dichroic beam splitter configured and disposed to reflect at least a portion of the focused light to the second measurement reflector and transmit at least a portion of the focused light to the first measurement reflector. The processor is configured to analyze light intensities in the image to determine locations of regions in the eye relative to the reference point. The processor is configured to associate the light intensities in the image with regions from which the light associated with the light intensities was scattered. The processor is configured to determine locations of a supra-nucleus, a nucleus, and a cortex of the eye. The system further includes a display coupled to the processor wherein the processor is configured to cause the processor to display an ellipse in the image. The processor is configured to adjust a size and position of the ellipse relative to the image. The processor is configured to analyze light intensities in the image to determine a location of an iris of the eye and to size and position the ellipse over the iris in the image. The processor is configured to adjust the size of the ellipse in response to input from a user of the system.

In general, in another aspect, the invention provides a system for performing fluorescent ligand scanning on a subject's eye. The system includes a light source configured to transmit light toward the subject's eye, a first microscope objective configured and disposed to focus light sent from the source toward the subject's eye to produce a focused spot of light to impinge the eye, an actuator coupled to a movable first lens and configured to position the focused spot of light sent from the first microscope objective through the movable first lens within the subject's eye, a lens configured to focus light sent from the source and scattered by the subject's eye, a photomultiplier tube or similar detector configured and disposed to receive a first portion of the received light and configured to provide indicia of an image corresponding to the first portion of the received light, and a processor coupled to the photomultiplier tube or similar detector and configured to analyze intensities of light in the image to determine a location of a reference point corresponding to an interface of a portion of the eye.

Implementations of the invention may include one or more of the following features. The light scattered by the subject's eye and received at the photomultiplier tube detector travels along a substantially similar path as the light sent from the source. The first microscope objective is removed to allow the light source to transmit light as a collimated beam toward the subject's eye.

Further, implementations of the invention may include one or more of the following features. The system further includes a second lens configured to focus light sent from the source and scattered by the subject's eye, a detector configured and disposed to receive a first portion of the received light from the second lens and configured to provide indicia of an image corresponding to the first portion of the received light, and the processor is further coupled to the detector and configured to analyze intensities of light in the image to determine a location of a reference point corresponding to an interface of a portion of the eye, wherein the light scattered by the subject's eye and focused by the second lens, travels along a path that is 45 degrees to the line of sight of the subject and 90 degrees with respect to the path of light from the source.

Also, implementations of the invention may include one or more of the following features. The system further includes a first dichroic beam splitter disposed in the path of light received by the second lens and at least a second dichroic beam splitter disposed in the path of light from the source, the first and at least second dichroic beam splitters configured to reflect at least a portion of light received to a detector. The system further includes a fast shutter disposed at a point in the path of the light as it travels from the light source toward the subject's eye. The system further includes a heart-rate monitor and the processor is configured to synchronize data collection to rest periods between heart beats. The heart-rate monitor is configured as a portion of a forehead rest for the subject. The heart-rate monitor is configured as a portion of a chin rest for the subject. The system further includes a pacemaker configured to regulate heart beats of the subject and the processor is configured to synchronize data collection to rest periods between heart beats.

In accordance with implementations of the invention, one or more of the following capabilities may be provided:

A workable fluorescence intensity measurements system (e.g., FLS) capable of localized measurements in the lens' of eyes.

A workable, quasi-elastic and/or light scattering intensity scan system for detection of diseases using measurements of eyes.

Diagnostic measurements of the eye can be taken by a single operator using a single device. Diagnostic measurements of the eye, e.g., for disease related information, can be obtained without physical contact with the eye.

Repeatable, highly accurate, measurements of light scattering intensity within an eye can be performed.

Fluorescent ligand scanning (FLS) and quasi-elastic light scattering (QLS) (also known as dynamic light scattering, self-beat spectroscopy, homodyne spectroscopy, laser Raleigh scattering and other names) can be performed on a single platform/device.

Movement in a subject's eye can be compensated for during diagnostic measurements.

Measurements for intra-ocular implants can be determined in a non-invasive manner, e.g., for Lasik operations. Infrared (IR) photo documentation of fluorescence intensity relative to position within an eye can be obtained.

The location within an eye of light scattering measurements can be accurately determined.

Quality control can be provided to verify the location within an eye for measured data.

Biomorphometrics of the eye can be determined, for example parameters for use in lens equations, measurement of the depth of the anterior segment, thickness of the cornea, and/or thickness of the lens.

Measurements can be made of aggregation in the eye relevant, e.g., to cataracts, molecular age, diabetes mellitus, radiation exposure, (e.g., for airline pilots, radiation workers, astronauts, cancer patients) and/or ocular toxicity (e.g., for long term exposure to systemic steroids and/or anti psychotic agents).

Neurodegenerative diseases and/or TSEs can be diagnosed and prognoses provided.

Drug testing can be performed, e.g., preclinical and clinical mammalian testing.

Movement in a subject's eye due to heart beat can be compensated for during diagnostic measurements.

A continuous cross-section scan of the eye can be performed.

The region of measurement of the eye may be sufficiently illuminated while maintaining eye safe levels of illumination at the retina.

These and other capabilities of the invention, along with the invention itself, will be more fully understood after a review of the following figures, detailed description, and claims.

BRIEF DESCRIPTION OF THE FIGURES

FIG. 3 is a cross-sectional image of an eye provided by the system shown in FIG. 1 with both pencil and fan beam lasers turned on.

FIG. 4 is a cross-sectional image of an eye provided by the system shown in FIG. 1 with only a pencil beam laser turned on.

DETAILED DESCRIPTION OF PREFERRED EMBODIMENTS

Some embodiments of the invention provide techniques for measuring light scattering within a subject's eye, e.g., a human eye, for diagnostic purposes. For example, a light scattering system includes a laser assembly that shines a laser beam into a subject's eye. A transfer lens focuses the scattered laser forming an image on a measurement mirror. Between the transfer lens and the measurement mirror the light is reflected from a steerable mirror that can be adjusted to position the image on the measurement mirror at a desired position. The measurement mirror has a pinhole that allows some of the scattered laser light to pass through and be detected by a single photon detector and analyzed by a hardware or software correlator. The scattered laser light not passing through the pinhole is reflected by the measurement mirror toward a charge-coupled device (CCD) camera. The camera obtains images of the scattered laser light and provides the images to a computer. The computer obtains information from the correlator and the images from the camera. The computer can analyze the output of the correlator (the correlation function) relating measured scattered light and position within the eye to determine whether the eye has indications of abnormalities such as diseases. The computer can further process the image information from the camera to provide images of the scattered light from the eye and to send control signals to the steering mirror to adjust for movement of the subject's eye and to help insure that light from a desired location of the eye is being directed through the pinhole of the measurement mirror. This light scattering system is exemplary, however, and not limiting of the invention as other implementations in accordance with the disclosure are possible.

Figure 1:
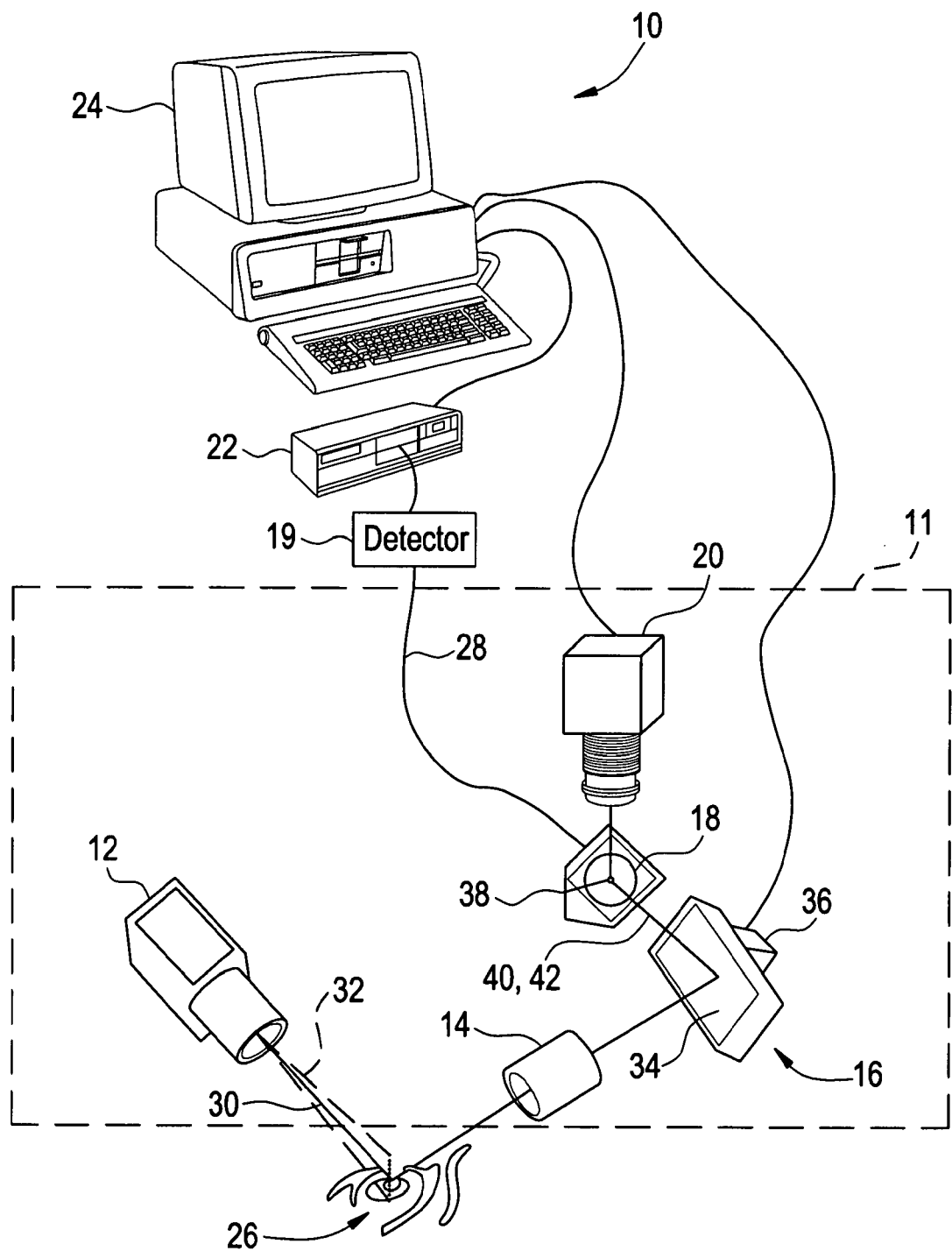
FIG. 1 is a prospective view of a light scattering system for use in measuring light scattering within an eye of the patient according to some embodiments of the invention.

Referring to FIG. 1, a light scattering system 10 includes a light source 12, a transfer lens 14, a steered mirror assembly 16, a measurement mirror 18, a CCD camera 20, a correlator 22, and a computer 24. The combination of the light source 12, transfer lens 14, mirror assembly 16, measurement mirror 18, and CCD camera 20 forms an optical unit 11. The optical unit 11 may be moved as a single unit in aligning the instrument to a subject's eye 26. The system 10 is configured to send beams of laser light into the subject's eye 26. Light scattered from the eye 26 is focused on the measurement mirror 18 at a position determined by the steering mirror assembly 16. Some of the light incident upon the mirror 18 passes through a small hole 38 to an optical fiber 28 which conducts the light to a photon detector 19. The detector 19 can output pulses to the correlator 22 for analysis, correlation can also be done in software, without specific hardware correlator or a combination of software and hardware. Other portions of the scattered light are directed from the mirror 18 to the CCD camera 20 and images of the scattered light region are provided to the computer 24. The computer 24 can also receive correlation functions and intensity measurements of the light received by the correlator and process the correlation functions and intensity measurements to perform diagnostic tests to determine likelihood of diseases and types of diseases in the subject, and to control the redirection of light by the steered mirror assembly 16 to control the location in the eye 26 from which light is being measured and provided to the correlator 22. While not shown, the system 10 includes a chinrest and a forehead rest to help position a subject's head such that the subject's eye 26 is positioned to be illuminated by the light source 12, with minor adjustments to the light source's position and/or angle as appropriate.

The light source 12 may be configured to provide multiple laser beams to the eye 26. For example the source 12 may be configured to send a laser pencil beam 20 toward the eye 26 that will scatter portions of the pencil beam 30. The pencil beam 30 will penetrate deep into the eye 26 along a straight line and will be scattered to varying degrees by different materials within the eye 26. The laser source 12 may be further configured to provide a fan beam, or slit beam, 32 directed at the eye 26. The fan beam 32 is a very thin, planar beam that will also penetrate deep into the eye 26 and be scattered by various materials to differing degrees. The fan beam 32 is used to assist an operator in aligning the instrument 11 to the subject. During alignment, the eye illumination is changed from pencil beam 30 to fan beam 32 and back several times a second. During measurement, preferably only the pencil beam 30 is turned on.

The light of the laser beams 30, 32 is preferably of a wavelength that is not visible or only slightly visible to the patient such that shining the beams 30, 32 into the patient's eye 26 will not cause discomfort to the patient, which could result in the patient moving undesirably. Preferably, both of the beams 30, 32 have wave lengths between about 400 nm-820 nm.

The transfer lens 14 is arranged with its longitudinal axis perpendicular to the pencil beam 30 and the fan beam 32 (i.e., the direction of propagation of the beam 30, 32). The angle, preferably 90°, between the beams 30, 32 and the axis of the transfer lens 14 helps to reduce/minimize dimensions of the target region of scattered light received from the eye 26. The transfer lens 14 is configured to focus the light scattered from the eye 26 onto the measurement mirror 18. The steered mirror assembly 16 includes the mirror 34 and a mirror driver motor 36. The mirror 34 is configured, and the assembly 16 is positioned, such that the mirror 34 receives the focused scattered light from the transfer lens 14 and redirects this light in beams 40, 42, corresponding to the beams 30, 32, to a focused image of the scattering region on the measurement mirror 18.

The mirror 34 is connected to the driver motor 36 that is configured to adjust the angle of the mirror 34 in two axes in accordance with control signals received from the computer 24. The motor 36 is configured to drive the mirror 34 to direct the scattered light from the transfer lens 14 such that the light is incident upon the mirror 18 at a desired relative location (e.g., such that a desired portion of the scattered light passes through a hole in the mirror 18).

The measurement mirror 18 is configured and disposed to reflect light from the steered mirror assembly 16 to the CCD camera 20. The mirror 18 reflects scattered light from the mirror 34 such that the CCD camera 20 can receive reflected light from the beams 40, 42 for imaging scattered light from the eye 26. A hole 38 may be provided in the center of the mirror 18. This hole 38 is preferably a pin hole (e.g., about 50 μm in diameter). The hole allows light from the scattered beam 40 to pass through and be received by an optical fiber 28. The optical fiber 28 transfers indicia of the portions of the beam 40 that pass through the pin hole 38 to the detector 19, that provides electronic indicia to the correlator 22.

The detector 19 is connected to the measurement mirror 18 through the fiber optic cable 28. The detector 19 is configured to convert the light received from the cable 28 to electronic pulses, and to send the pulses to the correlator 22.

The correlator 22 is configured to receive electronic pulses from the detector 19 and is configured to analyze fluctuations in light intensity of the light received via the pin hole 38 over time. The correlator 22 is configured to perform auto-correlation algorithms using indicia of the received light intensities to determine sizes of protein aggregates in the lens of the eye 26. The correlator 22 is further connected to the computer 24 and configured to provide information to the computer 24 regarding the size of protein aggregates in the lens of the eye 26.

The CCD camera 20 is disposed and configured to receive light reflected from the measurement mirror 18 from the light beams 40, 42. The camera 20 is configured to be focused on the pin hole 38 and to provide an image of the reflected light that has been scattered by the eye 26. The camera 20 is configured to process the received reflected light to produce images showing a cross-section of the lens of the eye 26 due to light scattered from the fan beam 32 and the pencil beam 30. The camera 20 is further connected to the computer 24 and configured to provide information to the computer 24 regarding the images of the eye 26 for display by the computer 24.

The computer 24 is configured to receive information from the correlator and the camera 20 and process this information accordingly to collect desired information and perform diagnostic operations. The computer 24 can process indications of aggregate types and size from the correlator 22 to determine indications of disease. The computer 24 can process images of the eye 26 from the camera 20 and provide control signals to the assembly 16 to adjust the positioning of the mirror 34 to control which portion of the scattered light in the beam 40 is incident upon the pin hole 38.

Figure 2:
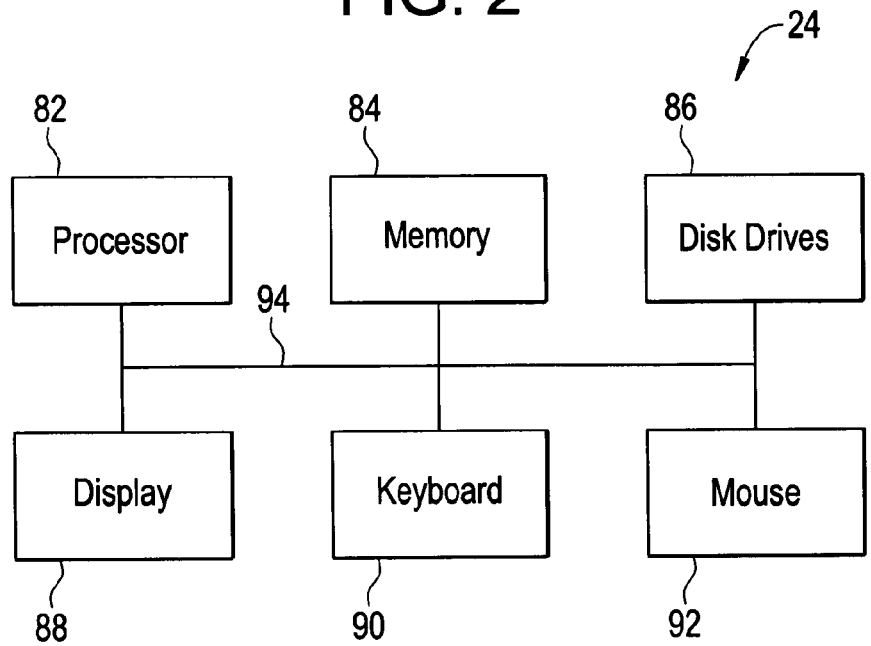
FIG. 2 is a block diagram of a computer shown in FIG. 1.

Referring also to FIG. 2, the computer system 24 includes a processor 82, memory 84, disk drives 86, a display 88, a keyboard 90, and a mouse 92. The processor 82 can be a personal computer central processing unit (CPU) such as those made by Intel® Corporation. The memory 84 includes random access memory (RAM) and read-only memory (ROM). The disk drives 86 include a hard-disk drive and can include floppy-disk drives, a CD-ROM drive, and/or a zip drive. The display 88 is a cathode-ray tube (CRT), although other forms of displays are acceptable, e.g., liquid-crystal displays (LCD) including TFT displays. The keyboard 90 and mouse 92 provide data input mechanisms for a user (not shown). The components 82, 84, 86, 88, 90, and 92 are connected by a bus 94. The computer system 24 can store, e.g., in the memory 84, software code containing computer-readable, computer-executable instructions for controlling the processor 82 to perform functions described below to image and analyze light scattered by the eye 26.

Figure 3:
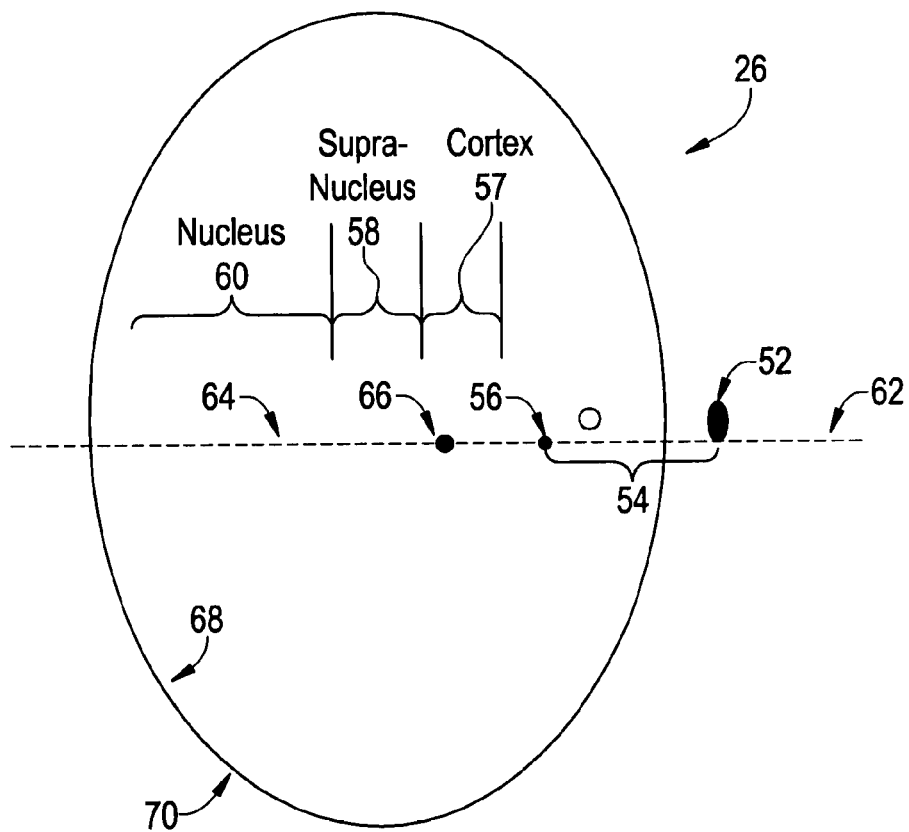
Figure 4:
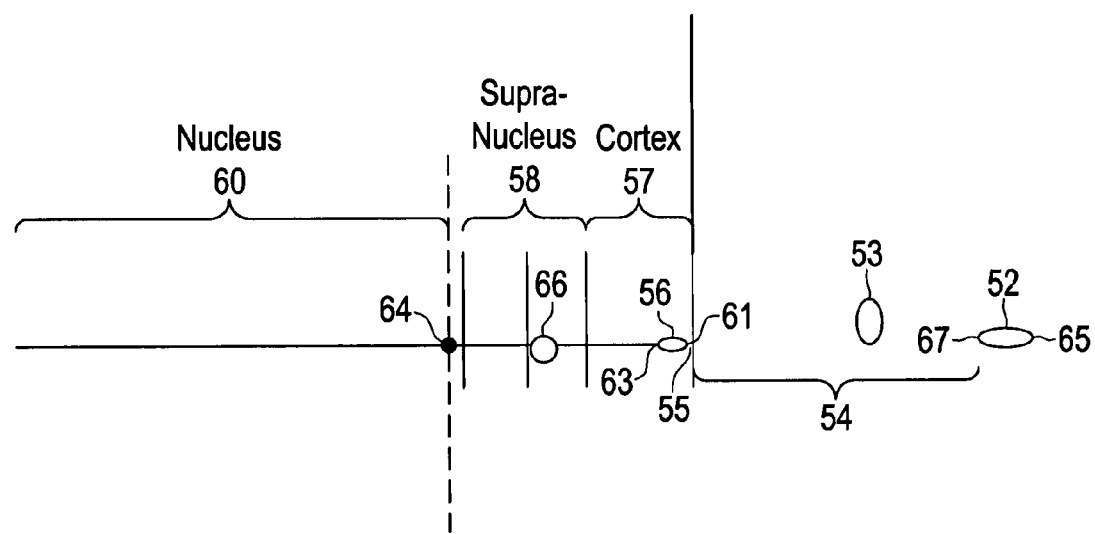

Referring also to FIGS. 3-4, the computer 24 is configured to produce an image 50 of the eye 26 from the scattered light of the beams 30, 32. As indicated in the image 50, light is scattered with significant intensity at a cornea and appears as a bright spot 52 in the image 50. As the pencil beam 30 further passes into the eye 26, light is not significantly scattered by a vitreous humor region 54 of the eye 26 and thus appears as a dark region in the image 50. Moving to the left in the image 50, light is significantly scattered by a lens capsule 56 due to Type IV collagens in the lens capsule, a supra-nuclear region 58, and a nucleus 60 of the eye 26. The significant scattering results in the bright portions shown in the image 50 due to the increased intensity of scattered light received by the camera 20. Also, a bright spot 53, the Purkinje spot, is caused by light reflecting from the cornea.

The camera 20 produces about 30 images/second, but one of skill in the art understands that other frame rates may also be used. Correlation functions are acquired in time frames between about one millisecond and one second. Typically, five correlation functions are obtained at each position in the eye 26 with the measurement 11 focusing on a given point in the eye. Normal motions of the eye 26 due to, e.g., pressure surges due to the heart beat of the subject, as well as other factors, typically cause the eye 26 to move during the time used for obtaining information to produce the correlation function. Such motion can reduce the effectiveness of the data produced and thus the effectiveness of the measurement taken, and consequently the diagnostic results. The system 10, and in particular the computer 24, is preferably configured to help stabilize the image 50 by compensating for motions of the eye 26.

When making measurements, preferably only the pencil beam 30 is turned on and the tracking mechanism is active. Referring to FIG. 4, the computer 24 can accommodate movement of the eye 26 due to various causes. For example, saccadic eye movements, blinking, pulsation (e.g., due to heart beats), or voluntary movements of the eye 26 can be accommodated using the tracking mechanism of the computer control signals and the motor 36. The computer 24 can determine the position where the laser beam 30 passes between two known regions to determine a reference point for use in locating specific portions of the eye 26 and for use in adjusting the mirror 34 in order to collect data through the pinhole 38 for a desired position of the eye 26. For example, the computer 24 can determine the location of an anterior lens capsule interface 61 corresponding to an interface between the lens capsule 56 and the vitreous humor region 54, a posterior lens capsule interface 63, an air-cornea interface 65, a cornea-aqueous region interface 67, a vitreous humor-retina interface, etc. For the interface 61, the computer 24 can determine the position where the laser beam 30 passes from the aqueous humor region 54 into the anterior lens capsule 56 by determining where the scattered intensity rises abruptly after the cornea 52 moving from right to left in the image 50. Any of the above mentioned interfaces can be used as a reference point for measurements, mapping and tracking.

The computer 24 places a marker, e.g., an "X" 55, at the location of the reference point, near the anterior lens capsule interface 61, in the captured image 50 to permit future visual confirmation of proper tracking operation. A pickup point 66 corresponding to the pinhole 38 remains at the same pixel address in the image 50. A desired pickup point 64 in the eye 26 is set in a setup screen to be a specified number of pixels measured from the lens capsule 56. Knowing the pixel position of the lens capsule 56, the desired pickup point 64, and the actual pickup point 66, the computer 24 can calculate the present error between the desired pickup point 64 and the actual pickup point 66 and move the mirror 34 to compensate for this difference. This operation is done 30 times a second (for example) to maintain the actual pickup point 66 at the desired position 64 in the eye 26. The computer 24 can determine the present position of the lens capsule 56 in this manner. The computer 24 can determine the distance in pixels from the present position of the lens capsule 56 to a desired position of the lens capsule 56 in the image 50. The determined distance is a horizontal distance (for example) from the present position of the eye 26 and its desired position relative to the field of view of the camera 20 and thus the image 50. The computer 24 can send control signals to the assembly 16 to cause the motor 36 to move the mirror 34 such that the actual horizontal position of the eye 26 in the image 50 is the desired horizontal position of the eye 26 in the image 50. The computer 24 continues to make these adjustments during measurements of the eye 26. The computer 24 can further determine the relative vertical distance between the present position of the eye 26 and its desired position and send control signals to the motor 36 to cause the motor 36 to adjust the mirror 34 to compensate for vertical motion of the eye 26. The computer 24 can analyze the information obtained over time and determine what information should be discarded due to movement of the eye 26 or blinking. The computer 24 can retain information not tainted by eye movement or blinking (or for which movement was sufficiently compensated) and discard information tainted by eye movement or blinking (and for which movement was not adequately compensated).

As part of the initial alignment procedure, the computer 24 may be further configured to superimpose an ellipse 68 on the image 50 with both laser beams 30, 32 turned on. The ellipse 68 is preferably sized and disposed to align with the pupil 70 of the eye 26. The ellipse 68 can be sized manually by a user of the computer 24 using, e.g., the keyboard 90 or the mouse 92. The user can use the image 50 to select borders between the various regions of the lens (cortex 57, supra nucleus 58, nucleus 60) and have data collected within each region. The user can select to insert or superimpose the ellipse 68 and move the image 50 of the eye 26 by moving the optical unit 11 with respect to the subject. When the optical unit 11 is positioned so that the ellipse 68 matches the pupil 70 of the eye 26 and the subject is fixating on a target (not shown), the laser beam 30 passes through a unique path in the lens of the eye 26 and measurements may be made at a position that is reproducible from one measurement session to another. The user can size the ellipse 68, e.g., by selecting the ellipse 68 and dragging a cursor to adjust the size in either axis of the ellipse 68. Using this alignment procedure, the same subject can be analyzed before and after various procedures, such as operations on the eye 26 or administration of medications, to evaluate the success of the procedures performed or medications administered on the subject.

The computer 24 may be further configured to separate the eye image 50 into regions. As shown in FIG. 3, the computer 24 can analyze the intensity of the image 50 and separate the image 50 into the cortex 57, the supra-nucleus 58, and the nucleus 60 regions of the eye 26. The computer 24 can use the segmentation of the eye image 50 to control the assembly 16 to determine the position of the measurement region 64. For example, the computer 24 can specifically choose to measure light scattered intensity of the supra-nucleus 58 or nucleus 60 regions. In particular, the computer 24 can cause measurements to be taken using the measurement region 64 at, e.g., four different depths within the eye 26 relative to the cornea 52.

The system 10 can be used to perform both quasi-elastic light scanning (QLS) and other forms of scanning on a single platform/device. For instance, an imaging agent can be introduced that will bind or attach to specific types of items, e.g., aggregates indicative of disease, and will react to light in a way that can be detected distinctively. Preferably, the imaging agent is configured to fluoresce in response to light, in which case the scanning is referred to as fluorescent ligand scanning (FLS). The imaging agent can be introduced into the eye in a variety of ways, e.g., through eye drops, creams, lotions, salves, systemically, etc. The light source 12 has the wavelength and polarization properties appropriate to the specific imaging agent. For example if the imaging agent is a fluorophor, then the wavelength is preferably tuned to the peak of the agent's absorption spectrum. The light source 12 can be tuned to the wavelength of light to which the imaging agent will react and the resulting image portion that passes through the pinhole 38 analyzed by the computer 24 such that the aggregates' presence and quantity can be determined. The imaging agent can take various forms such as a chromophor (that is colorimetric, in the visible light spectrum), a fluorophor (e.g., a fluorescent probe) that will fluoresce in response to light, or other material that will distinctively and detectably react to visible or non-visible (e.g., infrared) light. A distinctive reaction need not be unique, but is such that it differs (e.g., in wavelength and/or degree of reaction) from the reaction, if any, of materials in the region of interest other than the imaging agent. Fluorescing imaging agents preferably fluoresce different wavelengths of light than materials in the eye 26 and/or in amounts greater (at the fluorescent wavelength) than the materials is the eye 26. Exemplary fluorophors are discussed in U.S. Pat. No. 6,849,249 (herein incorporated by reference in its entirety), and include Chrysamine or Chrysamine derivative compounds such as {(trans, trans),-1-bromo-2,5-bis-(3-hydroxycarbonyl-4-hyrdoxy)styrlbenzene (BSB)}. The system 10 can also use the same camera 20 for both the QLS and FLS measurements. The system 10 can perform optical sectioning with FLS and the slit beam 32 to assist in mapping the eye 26 (e.g., sectioning the eye 26). The light scattered from the two beams 30, 32 can be co-registered on the image 50 as shown. Further, the computer 24 can use FLS measurements to confirm QLS measurements and/or can use QLS measurements to confirm FLS measurements and diagnostic conclusions.

Thus, the system 10 can be used for diagnostic purposes by contacting an ocular tissue of a mammal, e.g., a human subject, with a detectably-labeled compound which binds to an amyloid protein or pre-amyloid protein aggregate. The compound preferentially binds to amyloid proteins compared to other β-pleated sheet containing proteins. Preferably, the detectably-labeled compound contains a fluorescent probe. For example, the fluorescent probe or fluorophor is a Chrysamine or Chrysamine derivative compound such as {(trans, trans),-1-bromo-2,5-bis-(3-hydroxycarbonyl-4-hyrdoxy)styrlbenzene (BSB)}. Chrysamine G and derivatives thereof are known in the art (e.g., U.S. Pat. Nos. 6,133,259; 6,168,776; 6,114,175). These compounds bind to Aβ peptides, but are not fluorescent. The diagnostic methods utilize a highly lipophilic fluorescent amyloid-binding Chrysamine G derivative to detect Aβ peptides in the eye. Bioavailable lipophilic fluorescent probes may also be used. Such fluorophors and probes are commercially-available, e.g., from Molecular Probes, Inc. Eugene, Oreg. Some dyes, e.g., X-34 or {(trans, trans),-1-bromo-2,5-bis-(3-hydroxycarbonyl-4-hyrdoxy)styrlbenzene (BSB)} (Styren et al., 2000, J. Histochem. 48:1223-1232; Link et al., 2001, Neurobiol. Aging 22:217-226; and Skrovonsky et al., 2000, Proc. Natl., Acad. Sci. U.S.A. 97:7609-7614) have been used to analyze brain tissue (but not eye tissue). These probes emit light in the blue-green range, thus the level of fluorescence, which is diagnostically relevant, exceeds the amount of human lens autofluorescence in the blue-green range. Other useful compounds include a detectable methoxy agent such as Me-X04 (1,4-bis(4'-hydroxystyrl)-2-methoxybenzene). Other methoxy agents include, e.g., Chrysamine or Chrysamine derivative compound such as {(trans, trans),-1-bromo-2,5-bis-(3-hydroxycarbonyl-4-hyrdoxy)styrlbenzene (BSB)}. Such compounds are described in Mathis et al., Curr. Pharm. Des., vol. 10(13):1469-93 (2004); U.S. Pat. Nos. 6,417,178; 6,168,776; 6,133,259; and 6,114,175, each of which is hereby incorporated by reference in its entirety. Nonspecific amyloidphilic probes such as thioflavin T, thioflavin S or Congo red dye may also be used.

The system 10, in particular, the computer 24, can provide photo documentation of measured results. The computer 24 can provide, for every FLS number obtained, an indication of where in the image 50 the light came from that was analyzed for determining the FLS number. In this manner, the computer 24 can document the region from which various FLS indications came from. The FLS number and the corresponding region of interest can then be used to determine whether the FLS number corresponds to a particular disease or other cause. Indications or FLS numbers indicating aggregates in one region of the eye 26 maybe be indicative of disease or other abnormality while the same FLS number in a different region of the eye 26 maybe innocuous. Therefore, the computer 24 preferably associates measured FLS numbers with corresponding regions within the eye 26 from which the measurements were taken to arrive at the FLS number.

The computer 24 may be further configured to analyze different portions of the eye 26 to determine distances between intensity peaks in the image 50. For example, the intensity peaks can be used to determine the depth of the eye 26, e.g., for use in selecting an intra-ocular implant, e.g., the size of an artificial intra-ocular lens (IOL) for implantation in the subject's eye 26. Thus, the system 10 can be used to determine the appropriate intra-ocular implant to use in a non-invasive manner. The system 10 can also be used to determine the depth of the anterior chamber, corneal and lens thicknesses, etc.

Figure 5:
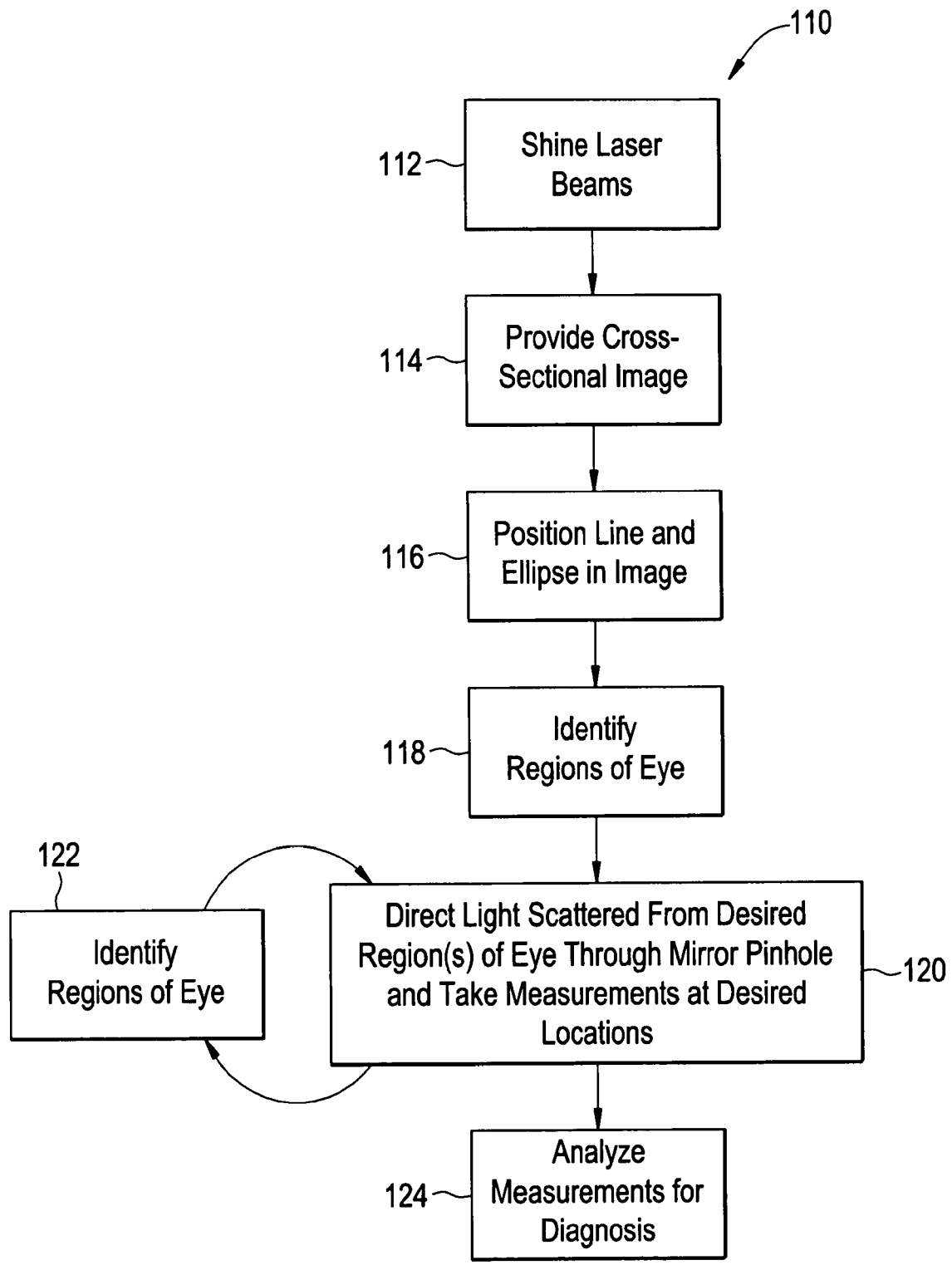
FIG. 5 is a block flow diagram of a process of measuring light scattering from a subject's eye using the system shown in FIG. 1.

Referring to FIG. 5, with further reference to the FIGS. 1-3, a process 110 for measuring and analyzing objects in the subject's eye 26 using the system 10 includes the stages shown. The process 110 can be used to perform FLS and/or QLS using the system 10. The process 110, however, is exemplary only and not limiting. The process 110 may be modified, e.g., by adding, removing, or rearranging stages.

At stage 112, the laser source 12 shines the laser's beams 30, 32 into the subject's eye 26. The beam 32 provides a plane of laser infrared light such that a cross section of the eye 26 can be imaged. The fan beam 32 will allow for the cross-section image 50 to be formed while the pencil beam 30 provides focused light for analyzing different regions of the eye for distinctive characteristics such as aggregates.

At stage 114, the light scattered by the eye 26 from the laser beams 30, 32 is imaged. The light scattered by the eye 26 is collected at preferably 90° relative to the incident beam propagation directions. The light scattered by the eye 26 is focused by the lens 14 on the measurement mirror 18. The measurement mirror 18 reflects the scattered light to the camera 20 that processes the received light to form the cross-sectional image 50 of the eye 26. The cross-sectional image 50 is a cross-section of the eye 26 with an overlay of the light scattered due to the beam 30. The cross-sectional image 50 is preferably of an anterior segment of the eye 26, including the cornea, the lens, and part of the nucleus of the eye 26. The image information is provided by the camera 20 to the computer 24 for display on the computer's monitor 88.

At stage 116, the ellipse 68 is positioned over the image 50 of the eye 26. The optical unit 11 can be positioned and the ellipse 68 can be sized manually by a user of the instrument 10. For example, the ellipse 68 is sized and the optical unit 11 is moved so that the ellipse corresponds with the pupil of the eye 26. The ellipse 68 can be repeatedly positioned on the eye 26 such that the process 110 can be repeated at different times on the same eye 26 and will allow for consistent measurement of the eye 26 such that measurement can confidently be taken for the same region in the eye 26 to compare changes in the eye 26 over time.

At state 118, various regions within the eye 26 are identified. This can be done manually by the user of the computer 24 manipulating input devices such as the keyboard 90 and/or the mouse 92 or automatically by the computer 24. If done automatically, the computer 24 analyzes the intensity pattern of the image 50 and identifies various regions of the eye 26 given known properties of intensity distributions of eye images. The computer 24 identifies the cornea 52 by moving along the direction of propagation of the beam 30 and finding a large high-intensity region in the image 50, and identifies the lens capsule 56 by moving toward the inner portion of the eye 26 in the image 50 and finding the next location where the image intensity is significant after a large region of low intensity. The computer 24 further sections the image 50 by identifying the cortex 57, the supra-nucleus 58 and the nucleus 60 regions by analyzing absolute and/or relative intensity levels scattered by the beam 32 along the line 62. The computer 24 stores indications of distances between the cornea 56 and the various regions within the eye 26, e.g., as indications of numbers of pixels between the various objects and regions of the eye 26.

At stage 120 the scattered light from the beam 30 is directed to the pin hole 38 in the measurement mirror 18 to measure desired regions of the eye 26. The computer 24 sends control signals to the motor 36 to drive and steer the mirror 34 to direct light scattered from the beam 30 from a desired region of the eye 26 to the pin hole 38. The computer 24 determines the desired region of the eye 26 from which measurements are desired to be taken. The computer 24 sends the control signals to the motor 36 to steer the mirror 34 in two axes such that the measurement region 66, corresponding to the pin hole 38, is positioned at the desired measurement region 64. The computer 24 can position the measurement region 64 at a set of desired regions within the eye 26, e.g., a set of four regions corresponding to different regions of the eye such as the cortex, two measurements within the supra nucleus, and one measurement within the nucleus. Other quantities of measurements and/or regions or distributions of measurements within the regions maybe used. Further, the computer 24 may position the measurement region 64 in a particular region or at a particular location to measure characteristics of the eye 26 at a particular position within the eye 26 for, e.g., diagnosing particular abnormalities. For example, the measurement region 64 can be placed at the supra-nucleus 58 to investigate for aggregates corresponding to Alzheimer disease, other neurodegenerative diseases, TSEs, etc. The scattered light received from the measurement region corresponding to the pin hole 38 is collected and transmitted through the fiber optic cable 28 to the detector 19 and the detected signal is sent to the correlator 22. The correlator 22 computes correlation functions to analyze the intensity of received light over time and provides indications of this analysis to the computer 24, e.g., for determination of abnormalities within the eye 26.

At stage 122, performed during the stage 120, the system 10 accommodates for motion of the eye 26. The computer 24 analyzes the image 50 to determine the location of a specific portion of the eye 26, e.g., the lens capsule relative to a desired location of the lens capsule 56 and sends control signals to the motor 36 to adjust the angle of the mirror 34 to accommodate for motion of the eye 26. Thus, the system 10 can provide a relatively stable image of the eye 26 and can take measurements from a relatively stable location within the eye 26 such that measured light intensity accurately reflects the existence or non-existence of aggregates and the type of aggregates within the desired tested location of the eye 26.

At stage 124, the computer 24 analyzes the measured results from the correlator 22 for diagnostic purposes. The computer 24 analyzes the data from the correlator 22 in conjunction with knowledge of the location of the measured regions 64 within the eye 26. Using this information, the computer 24 can determine the existence and type of aggregate or other objects within the eye 26 and provide indications, e.g., through the computer's display 88 to a user of the existence, non-existence, and/or type of object within the eye 26.

Figure 6:
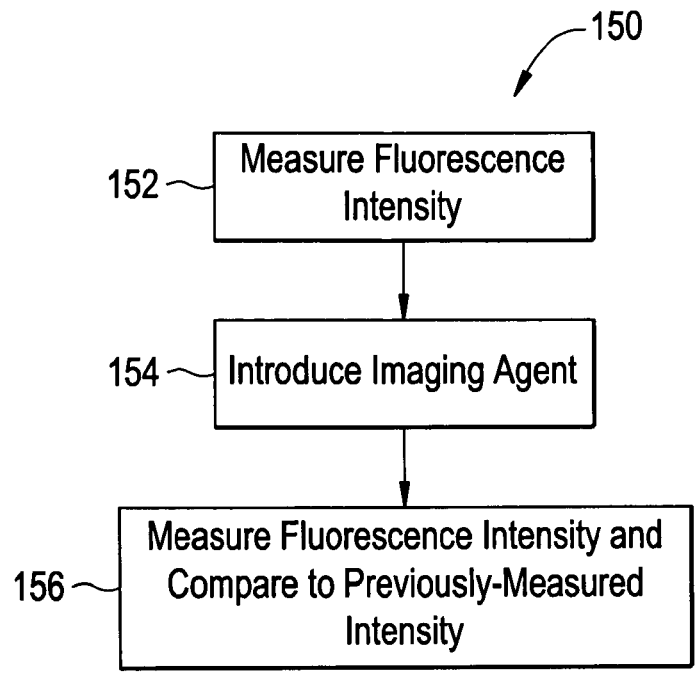
FIG. 6 is a block flow diagram of a process of performing fluorescent ligand scanning according to some embodiments of the invention.

Referring to FIG. 6, with further reference to the FIGS. 1-3, a process 150 for performing FLS on the subject's eye 26 includes the stages shown. The process 150, however, is exemplary only and not limiting. The process 150 may be modified, e.g., by adding, removing, or rearranging stages. For example, stage 152 may be removed and stage 156 modified to eliminate comparing measured intensity with previously-measured intensity. Further, while measuring fluorescence in response to light is discussed below, the process 150 could be modified to use other forms of energy and/or measure other characteristics, as discussed above.

At stage 152, the eye 26 is illuminated and fluorescence measured. The eye 26 is illuminated with a light source and fluorescence emitted from the eye 26 in response to the illumination measured and recorded. The magnitudes of emitted fluorescence and the locations of these magnitudes are correlated and recorded.

At stage 154, an imaging agent is introduced into the eye 26. The imaging agent is configured to bind to materials/objects of interest that may be present in the eye 26 and is configured to fluoresce in response to light from the source. The imaging agent may be introduced in a variety of manners, e.g., through drops applied to the eye 26, intravenously, etc.

At stage 156, the eye 26 is illuminated with light from the source and the fluorescence from the eye 26 measured. The intensity magnitudes and locations are correlated and stored, and compared with magnitudes recorded at stage 152, with magnitudes measured from similar locations in stages 152 and 156 being compared. The comparison includes analyzing differences in the magnitudes and determining presence of the material/object of interest, and amount of the material/object if indeed present in the eye 26. Conclusions can be determined regarding implications of the presence and/or amount of the material/object of interest such as a medical condition of the subject such as the existence and/or stage of a disease such as Alzheimer Disease.

Some embodiments of the system 10 may integrate both QLS and FLS technologies to enable non-invasive quantitative measurements of predetermined biological materials (e.g., one or more proteins) in the eye, to examine and measure deposits in specific areas of the lens for early detection of diseases (e.g., Alzheimer's disease). For instance, the system may be used to aid in the diagnosis (e.g., screening) of Alzheimer's disease by quantifying β-amyloid aggregates in the supranucleus region of the lens. To this end, QLS provides a quantitative measure of the relative amount of a material and/or object in the eye and FLS provides a visual identification of those where such material and/or object is located in the eye.

According to some embodiments, QLS and FLS measurements may be taken from the same anatomical region of the eye. By selecting a reference point on the cross-sectional image view, a galvanometer may be positioned (e.g., by software) for the 780 nm laser and a stepper motor may be positioned for the 405 nm laser to collect data at an anatomical location specified by the operator. The location may be defined as a 200 micron area surrounding the selected reference point.

Figure 7:
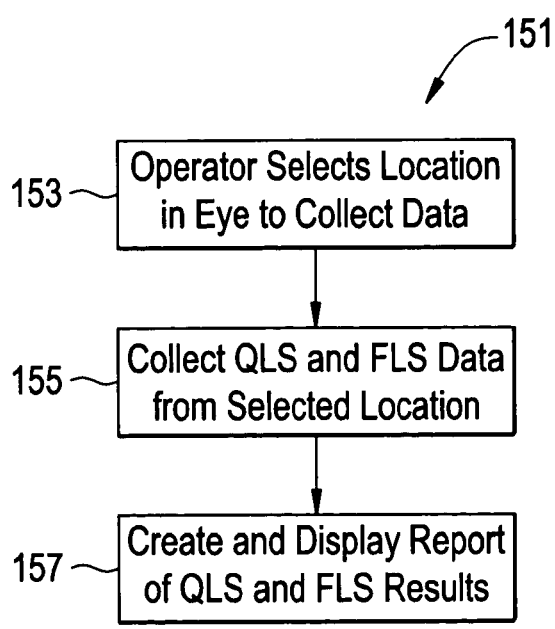
FIG. 7 is a block flow diagram of a process of performing quasi-elastic light scattering and fluorescent ligand scanning according to some embodiments of the invention.
Figure 8:
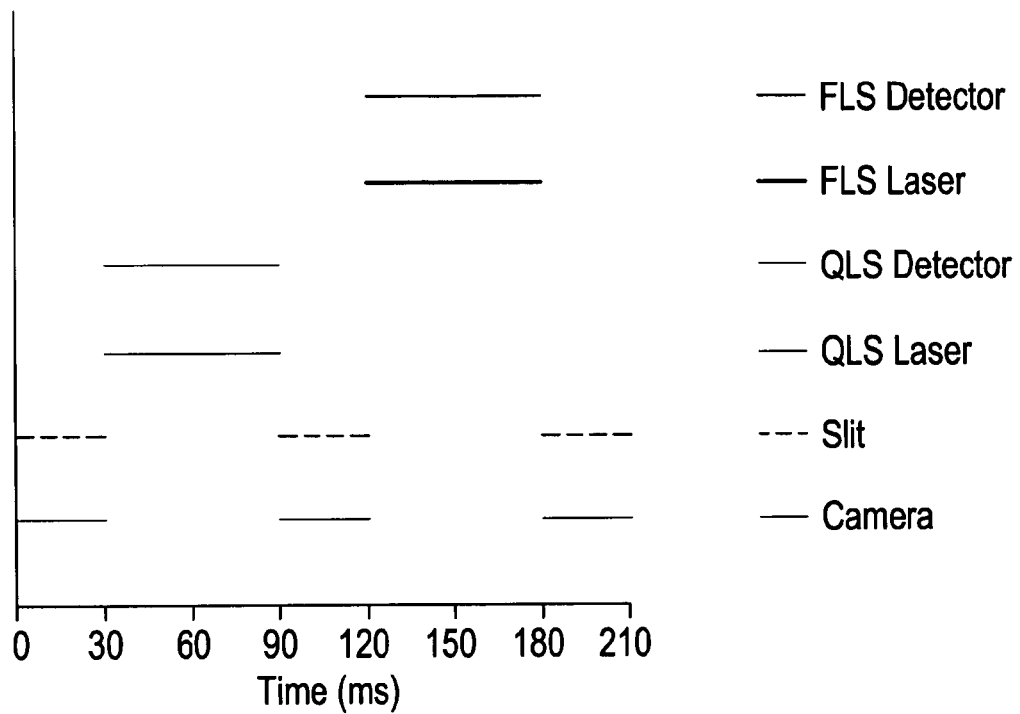
FIG. 8. is a diagram showing the timing of the acquisition of data according to some embodiments of the invention.
Figure 9:
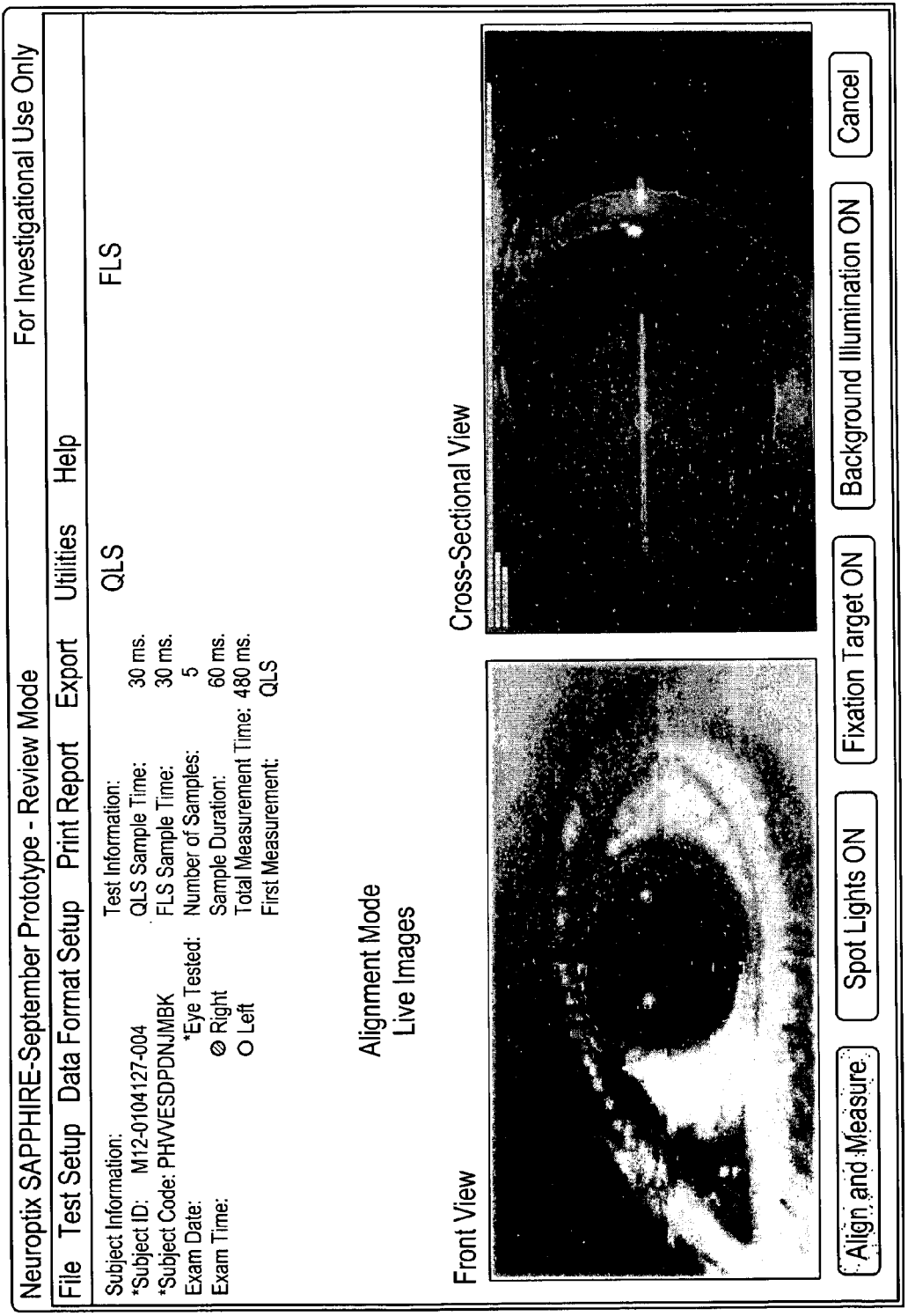
FIG. 9 is a sample display window showing test setting information and front and cross-sectional views of an eye according to some embodiments of the invention before performing quasi-elastic light scattering and fluorescent ligand scanning.
Figure 10:
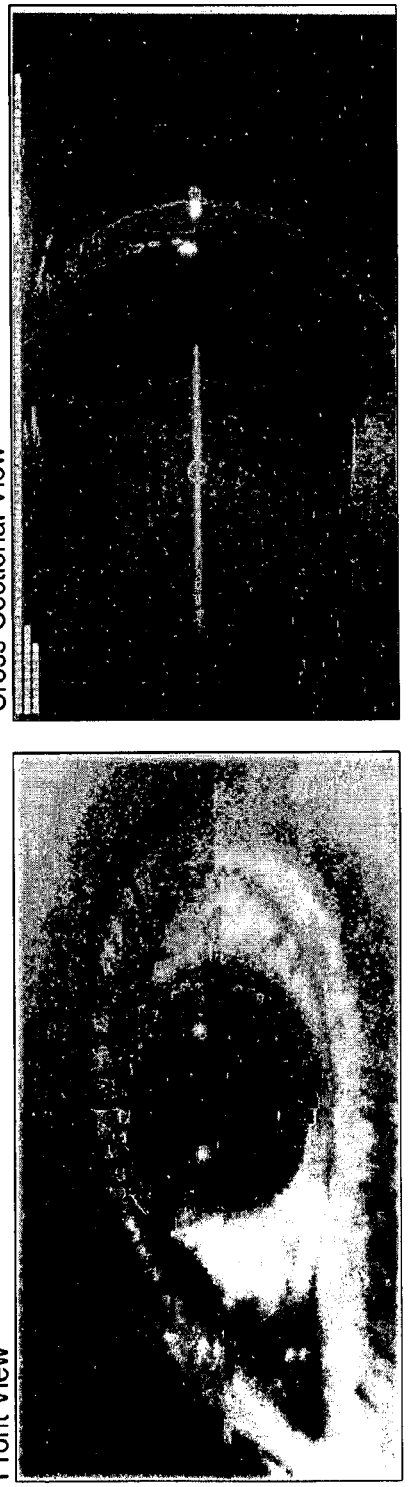
FIG. 10 is a sample display window showing measurements according to some embodiments of the invention after performing quasi-elastic light scattering and fluorescent ligand scanning.

Referring to FIG. 7, with further reference to FIGS. 8-10, a process 151 for measuring and analyzing objects in the subject's eye 26 using the system 10 includes the stages shown. The process 151 is performed using QLS and FLS technologies with the system 10. The process 151, however, is exemplary only and not limiting. The process 151 may be modified, e.g., by adding, removing or rearranging steps.

At stage 153, an operator may select an anatomical region (e.g., using keyboard 90 or mouse 92 to click on the cross-sectional image) of the eye 26 to be measured from front and/or cross-sectional views displayed on a display screen, as shown in FIG. 9. The anatomical region may be designated. At stage 155, data collection and measurement analysis begins. The location of the anatomical region may be recorded (e.g., via software processing) to mark (e.g., by superimposing the mark) on all cross-sectional images at the selected anatomical location. For front-view images, a circle may be superimposed (e.g., via software control) that is of a size similar to the pupil in the center of the image. Some embodiments of the system may collect 60 msec of data for at least one of QLS and FLS for each measurement cycle, as shown in FIG. 8. As many as ten measurements may be automatically taken in rapid succession without realigning the subjects. This allows the collection of several data sets without requiring retesting of a subject in the event that one or more data sets are contaminated due to subject motion. Selection of acceptable tests may be conducted manually by an operator prior to acceptance of the data set or automatically by a computer.

At stage 157, the system 10 provides a report of the QLS and FLS measurement results. Referring to FIG. 10, some embodiments may include software that provides a series of on-screen and/or printable reports of each measurement for operator review. The reports may comprise one or more of the test settings, the images associated with each measurement to define and characterize the location of data collection, the average QLS intensity ($I_{D\text{-}QLS}$) and average FLS intensity ($I_{D\text{-}FLS}$) for each data set, autocorrelation functions provided in graphical form for both QLS and FLS to evaluate for data set acceptance or rejection and curve fit parameters based on an exponential fit to the autocorrelation data, which, in some embodiments, may not be used in the analysis of data.

With regard to QLS, measurements of light intensities may be taken by collecting light intensities of photons from detector 19 in small time increments of, for example, 60 msec or less. By collecting light intensities from detector 19 at small time intervals, it is possible to calculate (e.g., using software) an autocorrelation function of the intensity over time. The autocorrelation function can then be used to calculate the relative size of particles present in a fluid matrix. In some embodiments, the autocorrelation function may be used to evaluate the quality of a QLS measurement since the autocorrelation function is sensitive to measurement artifacts, such as subject motion.

The average intensity over the measurement time in counts per second may be reported (e.g., via software). In some embodiments, these measurements may be analyzed separately in a spreadsheet format. In some embodiments, the primary QLS measure for analysis is the average intensity ($I_{D\text{-}QLS}$), in photons per second, of a wavelength of light captured by the detector 19 placed at a certain angle to an illumination source (e.g., light source 12). The wavelength of light may be, for example, 785 nm and the angle of incidence of the detector 19 may be 90 degrees to the line of propagation of the illumination source. Measurements may be taken in both the supranuclear and nuclear regions of the lens of the eye 26. The nuclear region of the lens does not express β-amyloid and thus acts as an internal control measure. A measure for statistical analysis is the ratio ($QLS_{Norm}$) between the average intensity ($I_{D\text{-}QLS\text{-}SN}$) of scattered light in the supranucleus region of the eye and the average intensity ($I_{D\text{-}QLS\text{-}N}$) of scattered light in the nucleus region of the eye:

$$QLS_{Norm} = \frac{I_{D-QLS-SN}}{I_{D-QLS-N}}$$

In some embodiments, the value of $QLS_{Norm}$ may directly correlate to disease state and as such will increase with increasing clinical disease state (i.e., increased amount of material and/or object aggregation in the eye). That is, if scattered light intensities increase over time, a potential diagnosis can be made, enabling clinicians and/or physicians to track the progress of disease in a patient by measuring intensity levels of scattered light reflected by the eye. In addition, increases in scattered light intensity may also enable clinicians, physicians and/or researchers to monitor the efficacy of drugs for a disease in clinical trial settings.

With regard to FLS, measurements may be taken by collecting counts of photons at a fluorescent emission peak and excluding other wavelengths by, for example, band-pass filtering. Exemplary compounds for binding to β-amyloid proteins include without limitation Methoxy-X04 and Methoxy X-34, which have peak absorption spectrums of 480-520 nm. By collecting light intensities from a detector 19 at small time intervals, the system 10 is capable of calculating an autocorrelation function of the fluorescence intensity over time.

The average fluorescence intensity over the measurement time in counts per second may be reported by either visual display or printing. The measurements may also be analyzed separately in spreadsheet format. In some embodiments, the primary FLS measure for analysis is the average intensity ($I_{D\text{-}FLS}$), in photons per second, of a wavelength of light captured by the detector 19 confocally aligned to the focus of the FLS illumination source (e.g., light source 12). The wavelength of light may be, for example, 480-520 nm. Measurements may be taken in both the supranuclear and nuclear regions of the lens of the eye 26. The nuclear region of the lens does not express β-amyloid and thus acts as an internal control measure. A measure for statistical analysis may thus be the ratio ($FLS_{Norm}$) between the average fluorescence intensity ($I_{D\text{-}FLS\text{-}SN}$) from the supranucleus region of the eye and average fluorescence intensity ($I_{D\text{-}FLS\text{-}N}$) from the nucleus region of the eye:

$$FLS_{Norm} = \frac{I_{D-FLS-SN}}{I_{D-FLS-N}}$$

In some embodiments, the value of $FLS_{Norm}$ may directly correlate to disease state and as such will increase with increasing clinical disease state (i.e., increased amounts of material and/or object aggregation in the eye). In other words, if fluorescence increase over time, a potential diagnosis can be made, enabling clinicians and/or physicians to track the progress of disease in a patient by measuring levels of fluorescence. In addition, increases in fluorescence may also enable clinicians, physicians and/or researchers to monitor the efficacy of drugs for a disease in clinical trial settings.

Additional embodiments may include determining the difference between the measured fluorescence intensity prior to administration of an imaging agent (e.g., ligand) to the eye 26. More specifically, the eye 26 may first be illuminated with a light source and the magnitude of intensity ($I_{Baseline}$) of fluorescence emitted from the eye 26 in response to the illumination may be measured and recorded. An imaging agent configured to bind to materials and/or objects of interest that may be present in the eye 26 and configured to fluoresce in response to the illumination may be introduced to the eye 26. One location of the eye into which the imaging agent may be introduced is the supranucleus region of the lens of the eye 26. When the eye 26 is illuminated with a light source, a magnitude of intensity ($I_{Imaging\ Agent}$) of fluorescence emitted from the eye 26 in response to the illumination may be measured and recorded. In some embodiments, a measure for statistical analysis may thus be the difference ($I_{DIFF}$) between these two intensities:

$$I_{DIFF} = I_{Imaging\ Agent} - I_{Baseline}$$

In some embodiments, $I_{Imaging\ Agent}$ may be the measurement or magnitude of intensity of fluorescence emitted from the eye 26 within 24 hours after the washout of bound agent has occurred. Furthermore, in some embodiments, the measurement may take place in the supranucleus region of the lens of the eye.

Some embodiments may include additional measures for evaluating the accuracy and utility of QLS and FLS measurements as measures of biological material, for example, β-amyloid, accumulated in the eye. One embodiment may be a combined measure to link both QLS and FLS measures in a combined metric. This analysis may be employed to address the possibility of false positive or conflicting results. This is in view of the possibility that QLS may provide a more sensitive metric of disease progression (but not of disease type) and that FLS may provide a sensitive measure for the presence or absence of β-amyloid (a selective marker of Alzheimer's disease). The combined measure $N_x$ may be calculated as the product of $QLSN_{Norm}$ and $FLS_{Norm}$:

$$N_x = QLS_{Norm} \times FLS_{Norm}$$

In addition, linear and multi-tau autocorrelation algorithms may be employed in some embodiments to graph intensity data across a specified time period for operator interpretation of measurement "quality." Previous clinical studies of QLS have found that the correlation function is a sensitive measurement of motion artifact during data collection. A curve may be fitted in user selectable "fast" and "slow" regions of the correlation function based on the equation $y(t) = Ie^{-kt}$ (e.g., using software), where I is the average intensity (amplitude), k is the decay time constant (gamma). This analysis may be useful in the determination of disease state.

Moreover, in some embodiments, each measurement may consist of up to 10 groups of 60 msec QLS and FLS measurements (a total of 120 msec in measurement per group). Each measurement group may be separated by a 30 msec image acquisition to define the location of measure. The combination of images and measurements may define each test. The tests, including average values, autocorrelation functions and images, may be reported to and evaluated by the operator. A measurement may be anticipated to yield at least five acceptable measures to be included in the data set.

In some embodiments, time course measurements for the initial pilot study may be reported as an X-Y scatter plot with time on the X-axis and each average intensity on the Y-axis. In addition, average and standard deviation for each subject, and groups at each time point will be reported. The optimal time for measurement following the application of an imaging agent may be chosen as the time which provides the greatest separation in $FLS_{Norm}$ and $N_x$ between normal and disease groups. This time may then be used in later studies to standardize test methods.

In some embodiments, each subject may be tested with both QLS and FLS without an imaging agent. This data may provide a control for comparison with QLS measurements following application of the agent. A hypothesis is that the agent may not affect QLS measurements which should remain consistent throughout the time course of measurements for each subject, independent of the imaging agent status. Mean values of $QLS_{Norm}$ within and between subjects may be evaluated using non-parametric signed-rank tests to evaluate this data for differences between QLS measures with and without imaging agent.

The system 10 has wide applicability for different diagnostic purposes. For example, the system 10 can be used as described above to determine aggregates for diagnosing various types of disease or other types of abnormalities within a subject.

The system 10 can further be used to determine the depth of a subject's eye for use in selecting a size of an intra-ocular implant, e.g., an artificial intra-ocular lens, to be inserted into the subject's eye.

Further, the system 10 can also be used to perform FLS and/or QLS without using anesthesia. The use of anesthesia on animals inhibits the ability to perform QLS due to dehydration of the eye in non-human animals under anesthesia. The system 10, however, can perform QLS without the anesthesia, thus improving the quality of measurements and diagnostic results from such measurements.

In some embodiments, a light source other than the laser source 12 can be used. For example, the light source may be a broad-spectrum light source that is essentially omni-directional (e.g., a light bulb), and/or that can provide a fan beam, and/or that can provide a pencil beam. One or more light sources may be used to provide one type of directionality, or combinations of different directionalities. Further, one or more energy sources that provide energy outside the light spectrum may be used in combination with an imaging agent that responds to energy outside of the light spectrum. For example, an imaging agent could be used that responds to microwaves, radio frequency energy, a magnetic field, etc. Multiple energy sources that collectively provide, or a single energy source that provides, energy both light and non-light energy may also be used in combination with one or more imaging agents that respond to the appropriate energy forms. While using these techniques may not result in the imaging agents fluorescing, these techniques can be considered as part of FLS.

Figure 11:
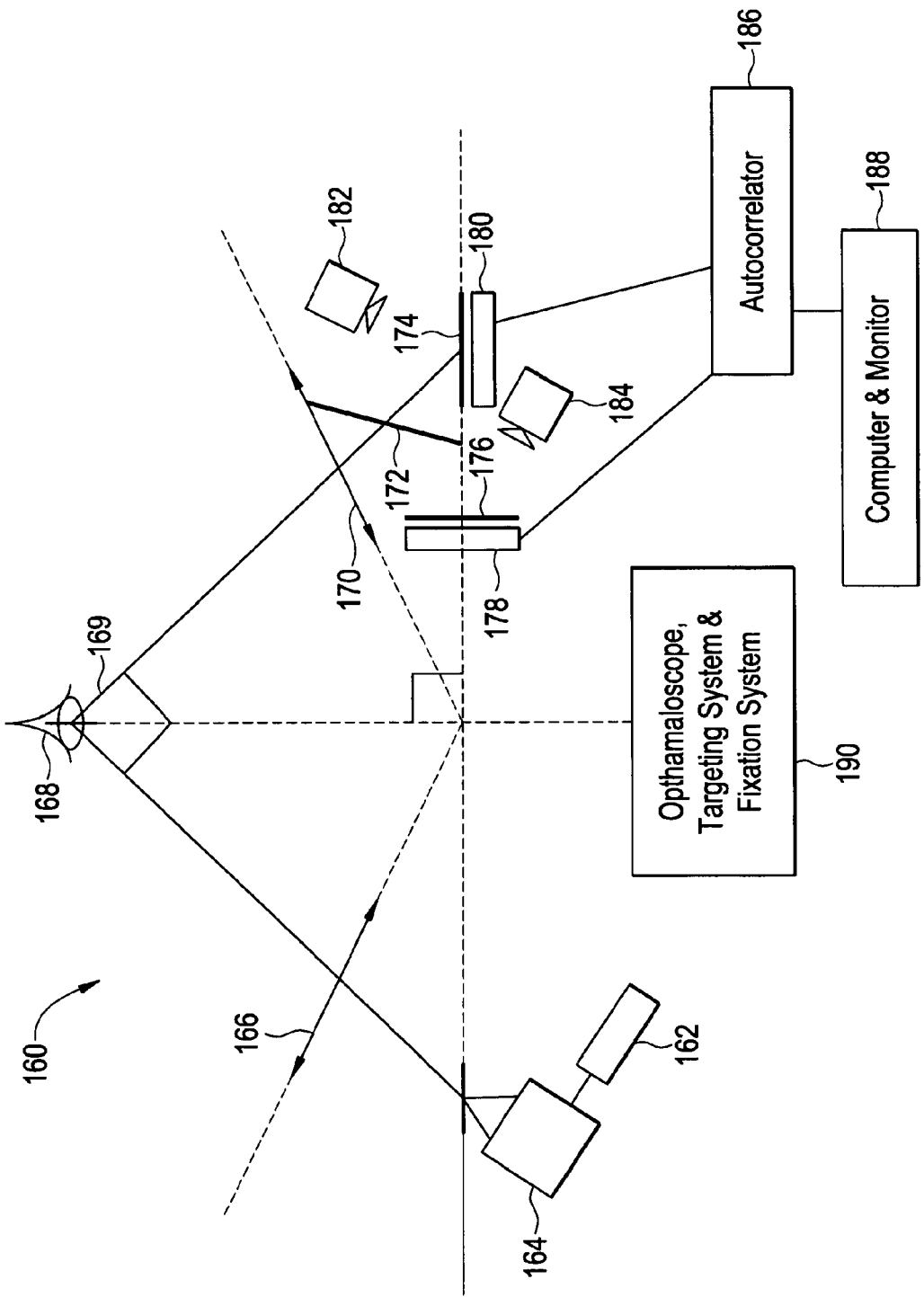
FIG. 11 is a block diagram of a scanning Scheimpflug illumination and scanning Scheimpflug imaging system for taking measurements within an eye of the patient according to some embodiments of the invention.

FIG. 11 illustrates a scheimpflug illumination and imaging system 160 according to some embodiments of the invention, which may include one or more (and preferably all) of the following: a light source 162, an optical scanning system 164, a pair of flat field lenses 166 & 170, a dichroic beam splitter 172, a pair of mirrors with a slit 174 & 176, a pair of detectors 178 & 180, a pair of CCD cameras 182 & 184, an autocorrelator 186, a computer and monitor 188, and a ophthalmoscope 190. The a scheimpflug illumination and imaging system 160 may be moved as a single unit aligning the system to the patient's eye with the ophthalmoscope 190. The system 160 is configured to send beams of laser light into a subject's eye 168, in which the light scattered from the eye 168 is focused on the mirrors with a slit on each 174, 176 by the second field lens 170 and the dichroic beam splitter 172. Some of the light incident upon each mirror 174, 176 may pass through the slit on each mirror to a QLS and FLS detector 180, 178 respectively.

At least one of the detectors 178, 180, and preferably both can output to the autocorrelator 186 for analysis. Other portions of the scattered light may be directed from the mirrors 174,176 to the CCD cameras 182, 184 respectively and images of the scattered light and fluorescence region may be provided to the computer 188. The computer 188 can also receive correlation functions and intensity measurements of the light received by the correlator and process the correlation functions and intensity measurements to perform diagnostic tests to determine likelihood of diseases and types of diseases in the subject. The computer control system preferably monitors several and preferably all aspects of the system through a customized graphical user interface (GUI). Image collection software may collect the images and store them in files for analysis (the files may be analyzed as previously disclosed). The ophthalmoscope 190 may be a standard ophthalmic head and chin rest for humans. The entire optical platform is positioned to the eye 168 through a Joy-stick control (for example). The range of motion is preferably sufficient enough to make measurements at any location in the anterior segments of both eyes. Custom holders may be adapted to or replace the head and chin rest for various animal studies of primates and rodents.

The light source 162 may be configured to provide a polarized laser beam which is preferably focused through a set of lenses and the optical scanning system 164 to produce a vertical fan beam of light. One of skill in the art will appreciate that the optical scanning system 164 may utilize one of several different methods for producing a linear sweeping motion (left and right across the page) of the light emission at the object plane of the first flat field lens 166.

The first flat field lens 166, which may contain multiple lens elements, is preferably tilted at an angle based on the Scheimpflug rule to create a virtual image plane that makes a vertical cross sectional plane 169 through the anterior segment of the patient's eye 168. The angle of incidence of the illumination is preferably 45 degrees to the line of sight of the patient. The optical scanning system 164 is used to sweep the vertical fan beam of light across the anterior segment of the eye 168. The angle of convergence should be fairly steep so that the angle of divergence is similarly steep. This exemplary configuration allows not only a sharp focal region within the cross sectional plane 169, but also insures that the light exiting from the back of the natural lens is similarly divergent and of low energy when it reaches the retina.

The scanning system 164 is preferably used to traverse the beam of light 10 mm (for example) into the anterior segment of the eye 168 beginning 1-2 mm (for example) in front of the cornea. While specific measurement values are given in this embodiment, they are exemplary only and not limiting. Single pass scan times of 16-33 msec (for example) through the eye can be made with a vertical fan beam of light. The focused vertical fan beam of light may be on the order of approximately 50 µm×10 mm (width by length) at the image plane 169. The power requirement is chosen to be eye safe. Real time power monitoring can be incorporated to ensure safety.

The second flat field lens 170 may be configured and/or disposed to image the scattered light at, for example, 45 degrees to the line of sight and 90 degrees with respect to the illumination as the vertical fan beam of light scanned across the anterior cross sectional plane 169 of the eye. The second flat field lens 170, which may contain multiple lens elements, may be tilted at an angle based on the Scheimpflug rule to create a sharply focused object plane which preferably coincides with the image plane of the illumination 169 of the patient's eye 168.

The dichroic beam splitter 172 may be configured and/or disposed to pass the excitation wavelength of the laser to a front surfaced mirror 174 with a slit aperture (for example) in the surface of the mirror. This preferably is the image plane for the QLS detection. The angle of incidence of the imaging is preferably 45 degrees to the line of sight of the patient. The QLS may be detected at the QLS image plane through a slit running horizontally (left and right in the plane of the page) with a width preferably on the order of 50 µm×10 mm (W×L) to maximize resolution and efficiency. A detector 180 (preferably a photomultimplier tube) may be behind the slit where its signals may be delivered to an autocorrelator 186 linked to a computer and monitor 188.

As the scattered image of the light fan beam is scanned across the slit, QLS measurements may be made with the detector 180 and autocorrelator 186. Sample times ranging from 50 nsec to 50 µsec (for example) may be made during the 3-33 msec (for example) scan. This allows resolution of a few hundred points. The information may be read into a file and analyzed by the computer 188. Alignment and summation of the cross sectional structures may be made through software algorithms.

The CCD camera 182 may be disposed and/or configured to receive light reflected from the mirror 174. The CCD camera 182 may be used to disqualify large eye movement, adjust for slit movement in the image, and show the cross sectional excitation image of the eye 168. The camera 182 may be further connected to the computer 188 and configured to provide information to the computer 188 regarding the images of the eye 168 for display by the computer 188. The cross sectional camera may be a Charged Couple Device (CCD) or Complementary metal-oxide-semiconductor (CMOS) device. Autocorrelation functions graphically presenting the fast and slow components of the light scattering analyses may be made as well as estimates of hydrodynamic radii (proxy for molecular size and molecular weight) derived from the slope determinations.

The QLS measurement is a line scan through the cornea. In other embodiments two dimensional scans may be made by scanning the slit up and down across the cross sectional image or by placing another scanning device between the object and image planes or by rastering a single illumination point instead of the light fan beam.

Fluorescence Ligand Scanning (FLS) is an important second tool for determining the presence of amyloid aggregation. As the vertical fan beam of light is scanned across the anterior cross section plane of the eye 168, the ligand's flouresced light may be imaged at 45 degrees to the line of sight and 90 degrees with respect to the excitation illumination by a flat field lens 170. The field lens 170, which may contain multiple lens elements, is preferably tilted at an angle based on the Scheimpflug rule to create an object plane which coincides with the image plane of the illumination of the patient's eye 169. The fluoresced light may be imaged off a dichroic beam splitter 172 that reflects the emission wavelength of the ligand to a front surfaced mirror with a slit 176. This is preferably the image plane for the FLS detection. The angle of incidence of the imaging is preferably 45 degrees to the line of sight of the patient. The FLS may be detected at the FLS image plane through a slit running vertically (up and down in the plane of the page) with a width preferably on the order of 50 to 200 µm×10 mm (W×L) to maximize resolution and efficiency. A detector 178 (preferably a photomultimplier tube) may be behind the slit where its signals may be delivered to the autocorrelator 186 linked to a computer and monitor 188.

As the scattered image of the light fan beam is scanned across the slit in the mirror 176, FLS measurements may be made with the detector 178. Sample times ranging from 50 nsec to 50 µsec (for example) may be made during the 3-33 msec (for example) scan. This allows resolution of a few hundred points. The information may be read into a file and analyzed by the computer 188. Alignment and summation of the cross sectional structures may be made through software algorithms.

The CCD camera 184 may be disposed and/or configured to receive light reflected from the mirror 174. The CCD camera 184 may be used to disqualify large eye movement, adjust for slit movement in the image, and show the cross sectional emission image of the eye 168. The camera 184 may be further connected to the computer 188 and configured to provide information to the computer 188 regarding the images of the eye 168 for display by the computer 188. The cross sectional camera may be a Charged Couple Device (CCD) or Complementary metal-oxide-semiconductor (CMOS) device.

The FLS measurement is a line scan through the cornea. In other embodiments two dimensional scans may be made by scanning the slit up and down across the cross sectional image or by placing another scanning device between the object and image planes or by rastering a single illumination point instead of the light fan beam.

The cameras 182, 184 focused on the image planes of both the QLS and FLS image planes may provide cross sectional and fluorescence images respectively. The cameras 182, 184 may have frame rates of 30 to 60 fps (for example). Additionally, since the QLS and FLS slits in the mirrors 174, 176 act as fiducials across the images, these images provide feedback information of saccadic eye movement and occlusion (blinking) to enhance the accuracy and precision of the QLS and FLS measurements.

Calibration of the system 160 may be made using custom cuvettes filled with custom microspheres. Several concentrations of spheres and different size spheres may be utilized. Initial calibration may be with a square cuvette rotated preferably 45 degrees to the line of sight. This ensures that the faces of the cuvette are perpendicular to the incoming illumination and outgoing scattering. Additionally a second type of cuvette may be made with a tube within a tube. The radii and their positions preferably approximate the cornea and the interocular lens. The inner tube may be filled with microspheres and the outer tube may be filled with water.

Figure 12:
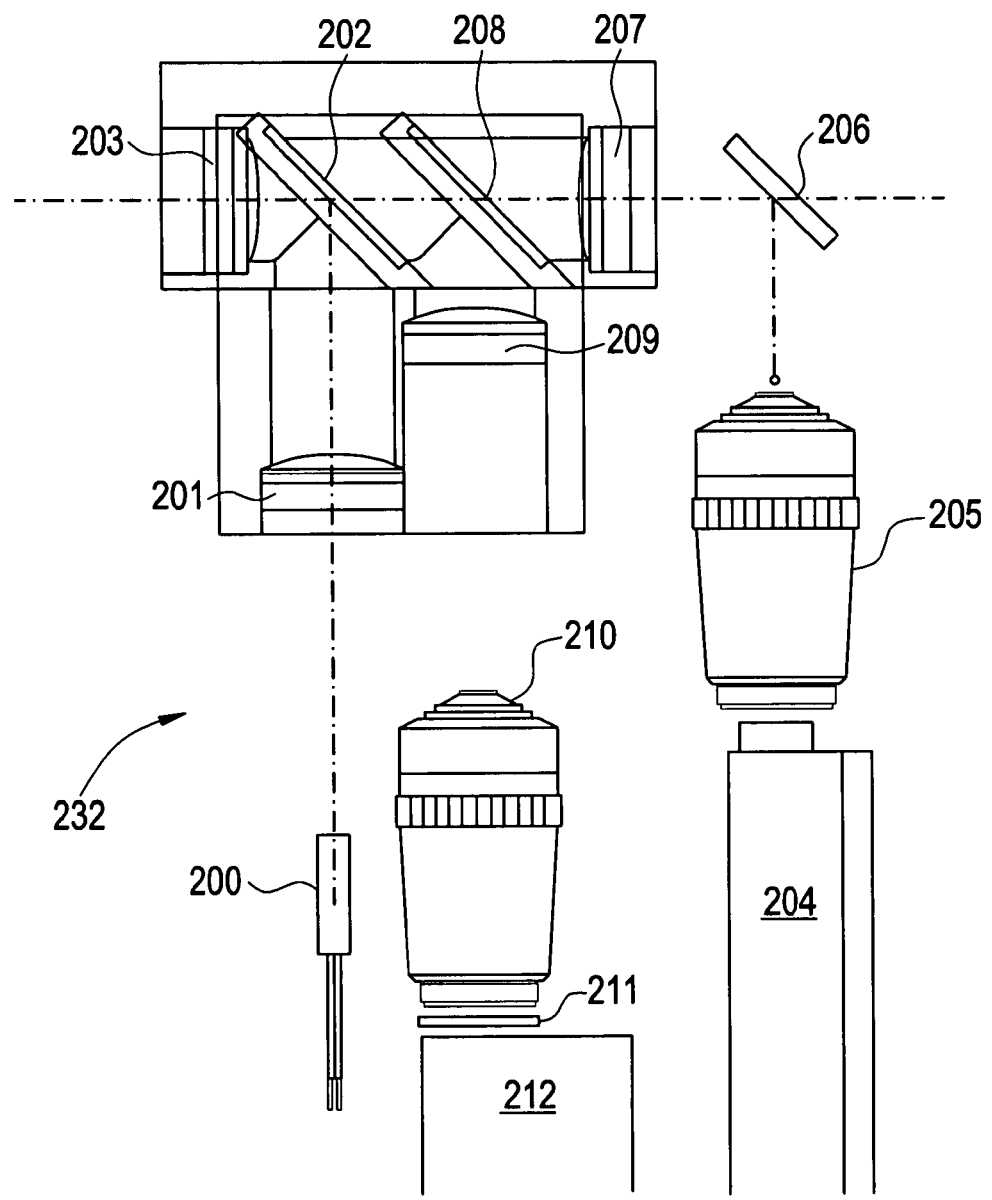
FIG. 12 is a side view of a portion of a light scattering system for use in measuring light scattering within an eye of the patient according to some embodiments of the invention.
Figure 13:
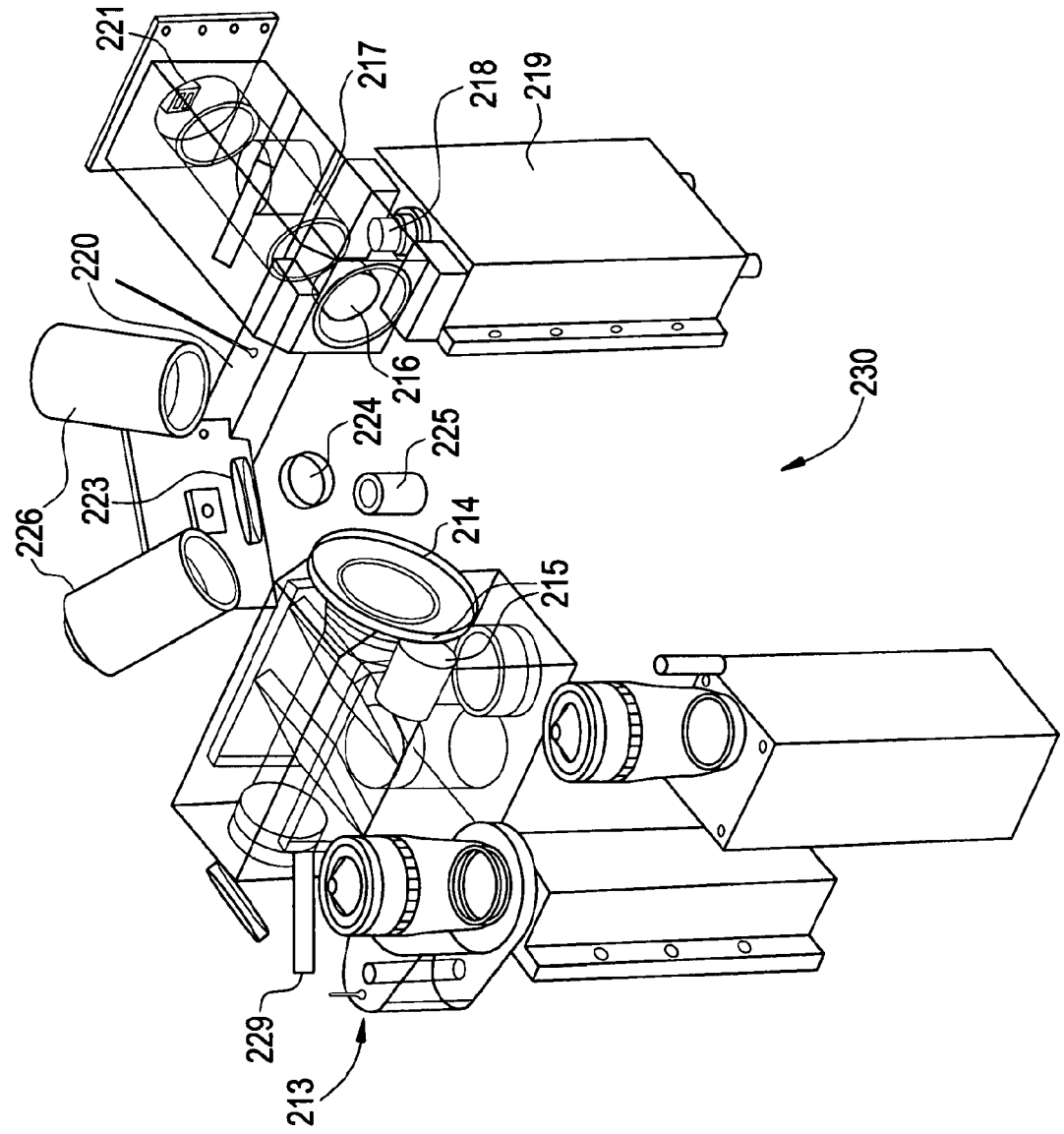
FIG. 13 is a perspective view of a light scattering system for use in measuring light scattering within an eye of the patient according to some embodiments of the invention.
Figure 14:
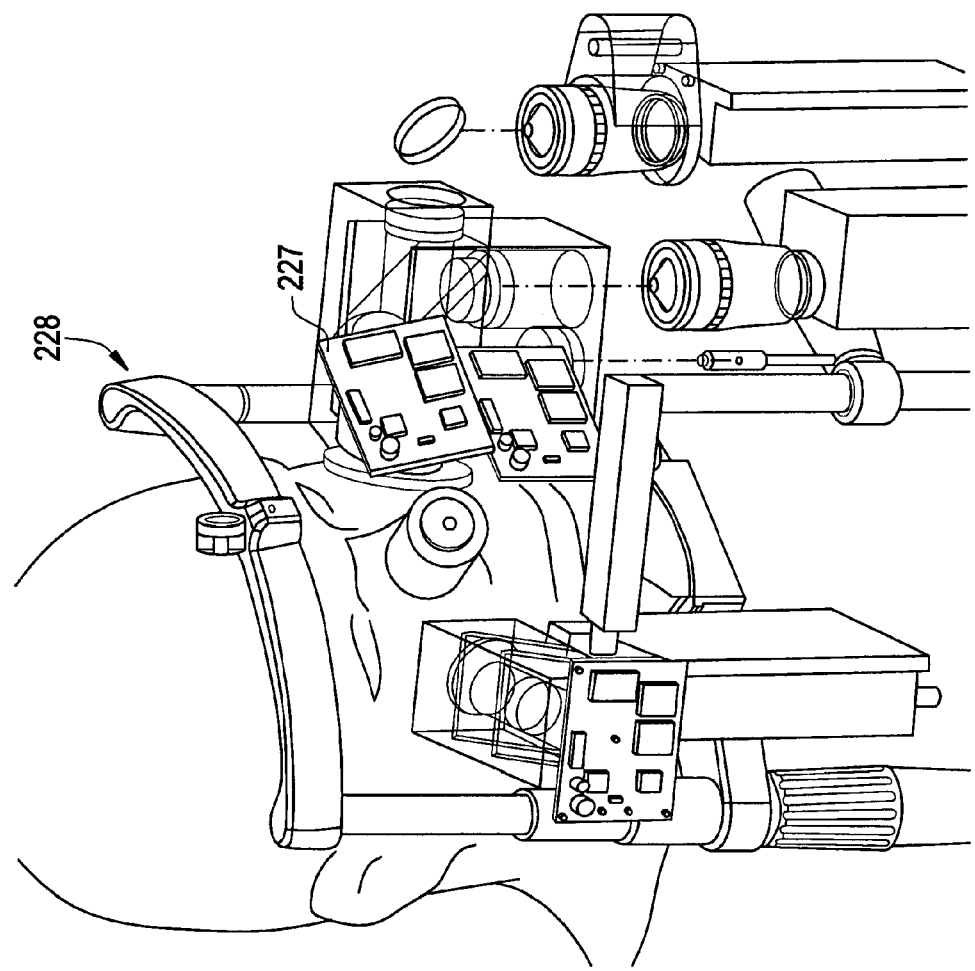
FIG. 14 is a perspective view of a light scattering system for use in measuring light scattering within an eye of the patient in relation to the head of the patient according to some embodiments of the invention.

Referring to FIG. 13 with further reference to the FIGS. 12 and 14, a light scattering system 230 according to some embodiments of the invention, which may include one or more (and preferably all) of the following: a first laser light source 200, a first lens 201, a first dichroic beam splitter 202, a second lens 203, a second laser source 204, a first microscope objective 205, a mirror 206, a third lens 207, a second dichroic beam splitter 208, a fourth lens 209, a second microscope objective 210, a light filter 211, a detector 212, a lens mount 214, a motor 215, a fifth lens 216, a third dichroic beam splitter 217, a slit aperture 218, a second detector 219, a second motor 220, a camera 221, a magnified view alignment camera 222, a fourth dichoric beam splitter 223, a second light filter 224, a narrow angle target 225, a crossed-spot alignment system 226, wide view alignment camera 227, and a stereotactic platform 228. The system 230 is configured to send beams of laser light into the subject's eye. Light scattered from the eye is focused onto the first and second detectors 212, 219.

The first laser light source 200 may be configured to provide a laser beam that can be directed to the eye. Preferably, the laser light source beam has a wavelength of about 780 nm. Light from the laser source 200 may be focused through the set of the first lens 201, first dichroic beam splitter 202, and second lens 203 to produce a spot of light that impinges the eye. The focused spot of light is on the order of 50 to 200 µm (for example) in diameter at the eye. The power requirement may be chosen to be eye safe. Real time power monitoring may be incorporated to ensure safety.

The second laser light source 204 may be configured to provide a laser beam that can be directed to the eye. Preferably, the laser light source beam has a wavelength of about 405 nm (for example). In the exemplary embodiment, excitation light from the laser source 204 may be used to accomplish FLS measurements. Light from the laser source 204 may be focused through the first microscope objective 205, to the mirror 206. The microscope objective 205 may be moved out of the optical light path through the use of a mechanism 213. The removal of the microscope objective 205 produces a collimated beam of light instead of a focused spot at the eye. Collimated light is light having rays that are parallel and thus includes a plane wavefront.

The mirror 206 may be configured and/or disposed to reflect the light from the microscope objective 205 through the lens 207, dichroic beam splitters 208, 202 and lens 203 to produce a focused spot of light that impinges the eye.

The fourth lens 209 may be configured and/or disposed to focus light reflected off of the dichroic beam splitter 208 through the microscope objective 210, and filter 211 to the detector 212. Preferably, the detector 212 is photomultiplier tube (PMT) type detector with a pinhole over its aperture, however, other types of detectors may be used. The aperture of the detector 212 may be the image plane for the FLS detection of the system 230. Although not shown, the detector's 212 PMT signals may be delivered to an autocorrelator (e.g., 186 in FIG. 11) linked to a computer and monitor (e.g., 188 in FIG. 11).

The lens mount 214 may be configured to hold the lens 203 and may be attached to the motor 215. The focused spot of light originating from the second laser source 204 may be scanned through the eye at preferably 45 degrees to the line of sight of the patient by movement of the motor 215 which may be attached to the lens mount 214. Thus preferably, the movement of the motor 215 causes the movement of the lens 203 along the axis of the light beam. The movement of the lens may change the location of focus and may result in the movement of the focused spot of light.

Choosing a focused spot to impinge the eye creates a cone of light within the eye, maximizing the light intensity at an anatomically desired location for fluorescence measurement, while allowing the laser energy to be dispersed over a wider area of the retina, which is positioned distal to the lens of the eye. This design allows more power to illuminate the region of measurement, while maintaining "eye safe" levels of illumination at the retina, which is prone to damage from excessive light exposure. Specific calculations for eye-safety are defined within ANSI Z136.1 "Safe use of Lasers."

As the focused spot is moved, in discrete steps (preferably), across the lens of the eye, the ligand's fluorescence may be backscattered and imaged back through the system through the lens 203, and the dichroic beam splitter 202, to reflect off the second dichroic beam splitter 208. The light reflected off of the dichroic beam splitter 208 as mentioned above may go through the lens 209 and may be imaged to a point by the microscope objective 210 through the light filter 211 to the detector 212 with a pinhole over its aperture.

The signal collected by the detector 212 can be used to perform several analytical techniques to describe the fluorescent behavior of the region of interest such as autocorrelation of light intensity over time to perform fluorescent correlation spectroscopy and total intensity and/or average intensity over a known measurement period can be performed to define gross signal level.

The fifth lens 216 may be directed and/or configured to focus the light scattered from the eye at preferably 45 degrees to the line of sight and 90 degrees with respect to the path of the illumination laser light beam from the source 200. The fifth lens 216 may focus the light onto the third dichroic beam splitter 217.

The third dichroic beam splitter 217 may reflect the light onto a slit aperture 218. The slit aperture 218 may be configured to allow light to pass through and be received by the second detector 219. This may be the image plane for the QLS detection. The angle of incidence of the imaging is preferably 45 degrees to the line of sight of the patient. The slit's 218 width is preferably on the order of 50 to 200 µm×10 mm (W×L) to maximize resolution and efficiency. Although not shown, the detector's 219 (APD, or similar sensitive light detector) signals may be delivered to an autocorrelator (e.g., 186 in FIG. 11) linked to a computer and monitor (e.g., 188 in FIG. 11).

The scattered image of the light beam may be scanned by translating the slit aperture 218 and the detector 219 with the motor 220. QLS measurements may be made with the detector 219 and an autocorrelator. The sample of a discrete location/volume can be on the order of 30-msec (one frame of video), then the optical system will scan to the next anatomical location of the eye for the next measurement, and so-on through the anatomical region of interest. A preferred method to measure from the lens capsule to cortex may include taking measurements in approximately 33-msec "steps" accounting for approximately 50 to 200-um volumes, stepping through the eye. A desirable feature is to allow this process to occur without significant eye movement (due to heart beat or other eye motion).

There is no limit as to how many times this process may be employed in a single QLS measurement session, so a measurement could be as short as a few millisecond or as long as 10's of seconds (for example) with repeated "scans" of many "steps" through the eye. Sample times ranging from 1 µsec to 200 µsec (for example) may be made during the scan. Scan speeds may be varied to capture the different anatomical features of the lens and post processed to account for movements due to a variety of reasons including heart beats, the eyes micro-saccades, etc. The information may be read into a file and analyzed by the computer. Alignment and summation of the cross sectional structures may be made through software algorithms.

The camera, or similar detector 221 may be disposed and/or configured to receive scattered light from the eye that travels through the dichroic beam splitter 217, providing an anatomical reference image. The camera 221 may be used to disqualify large eye movement, adjust for slit movement in the image and show the cross sectional excitation image. The camera 221 may be a Charged Couple Device (CCD), a Complementary metal-oxide-semiconductor (CMOS), or any other type of appropriate device for capturing images. Autocorrelation functions graphically presenting the fast and slow components of the light scattering analyses may be made as well as estimates of hydrodynamic radii (proxy for molecular size and molecular weight) derived from the slope determinations. The QLS measurement is a line scan through the cornea. Additional optical filters may be placed within the optical path to enhance signal to noise ratio of the detected signal.

The wide view alignment camera 227 may be configured to help a technician align the system 230 to a patient's eye. The camera 227 may allow the technician to coarsely align the patient.

The magnified view alignment camera 222 may be configured and disposed to provide a magnified view of the patient's iris as viewed through the beam splitter 223 and a filter 224.

Alignment of the system 230 may be done under Joy-stick control moving the entire optical system 230 to the left or right eye, up or down. The device can be manually aligned to the patient by the operator using a crossed-spot alignment system 226 that projects two spots that overlay each other on the apex of the cornea centered on the iris. Targets can be illuminated with colored light emitting diodes (LEDs) that may be visible to the eye and to the alignment cameras 222, 227. An infrared (IR) LED illumination scheme may be included to provide additional illumination for aiming.

A narrow angle target 225 may be configured and/or disposed to be reflected off of the beam splitter 223 and through the filter 224 to provide a spot target for the patient to fixate on with his or her vision. The target may be backlit by a red LED. The focus of the target 225 may be adjustable to account for the patient's dioptric correction. The spot target subtends approximately 2 degrees. In use, the patient may remove their glasses and the target 225 may be adjusted to their nominal average power prescription. The magnified view camera 222 may be bore-sighted with the fixation target 225 to provide a front view co-axial with the optical axis of the eye.

The stereotactic platform 228 may be a standard ophthalmic head and chin rest for humans. The entire optical platform may be positioned to the eye through the joy-stick control as described above. The range of motion may be sufficient enough to make measurements at any location in the lenses of both eyes. Custom holders may be designed to adapt to or replace the head and chin rest for various animal studies of primates and rodents.

As mentioned above, alternative measurement embodiments can be implemented via removing the microscope objective 205 with the mechanism 213 which can be actuated manually or with a motor. The removal of the microscope objective 205 from the optical path of the light from the light source 204 allows the excitation light from the source 204 to be emitted as a collimated beam. It is known in the art that collimation of lower quality lasers can be accomplished by the addition of appropriate collimating optics. In this embodiment format, the collimated pencil beam of light may transmit through the eye and impinge as a relatively collimated spot in the retina. With properly chosen detector and optics, this arrangement can supply sufficient illumination without requiring laser illumination at levels which are not eye-safe.

In this collimated beam configuration, both detectors 212, 219 may be employed to perform a number of measurements. The collimated pencil beam may be positioned across the lens of the eye, and the ligand's fluorescence may be backscattered and imaged back through the system for FLS measurements at the detector 212. The ligand's fluorescence is also emitted in all directions, and can be imaged at preferably 45 degrees to the line of sight and 90 degrees with respect to the illumination beam path by the lens 216. The light may be imaged off the beam splitter 217 onto the slit 218 with the detector 219 behind the slit for QLS measurements. The signal collected by this detector 219 can be used to perform several analytical techniques to describe the fluorescent behavior of the region of interest such as; performing QLS at 405-nm similar to the measurement done at 780-nm when a 405-nm narrow-pass filter is placed immediately prior to the detector, autocorrelation of light intensity over time can be done to perform fluorescent correlation spectroscopy, and total intensity and/or average intensity over a known measurement period can be performed to define gross signal level. FLS detection may also be made in this configuration with an appropriate change in filter selection.

In other alternative embodiments, the system 230 can be used to detect the fluorescent decay characteristics of the ligand, allowing an alternate method to isolate fluorescence due to ligand from other fluorescent sources, such as lens autofluorescence. This can be accomplished in part, by choosing a 405 nm laser source 204 with fast switching capability, or by placing a fast switch or shutter (such as a q-switch) 229 in the excitation beam path, or in the either detection path (as described above) and using any of the fluorescent detection paths described previously.

The optical measurements of the system 230 are critically sensitive to translational motions of the eye in excess of approximately 150-μm. In the original embodiments, a large source of motion artifact was eye motion induced by heartbeat associated motion. To avoid these predictable artifacts, a number of methods can be employed.

Computer algorithms can be utilized that recognize motion artifacts in either the position of anatomic structures in the slit-lamp camera 221, by evaluating the relative position of measurement volume in relationship to anatomic structures, or by evaluation of correlation functions, looking for hallmark characteristics of motion on this measure.

A second approach to avoiding motion artifact due to heartbeat, may be to synchronize data collection to heart beat. Resting heart rate in humans is typically 50-85 beats per minute [BPM], but can exceed 120-BPM in cases of pathologic tachycardia. By synchronizing measurement to the rest period between beats, this artifact can be avoided.

Methods to synchronize measurements to the rest periods between heart beats include:

i. Placing a heart-rate monitor on subjects and using subject heart rate to control start and stop of data acquisition, and to calculate the number and positional distribution of measurements through an anatomic region of interest. This could be done using any number of commercially available heart rate monitor signals or custom built.

ii. Building a heart-rate monitor into a convenient contact point of the device, such as forehead or chin rest and using subject heart rate to control start and stop of data acquisition, and to calculate the number and positional distribution of measurements through an anatomic region of interest. This could be done using any number of commercially available heart rate monitor signals or custom built, with appropriate location of electrodes.

iii. Constructing the system 230 with an incorporated pacemaker, and using the pacemaker to modulate both heart beat and data collection in an appropriate manner to insure clean data collection.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. A system for performing fluorescent ligand scanning on a subject's eye, the system comprising:
    a display screen showing an image of the eye to allow an operator to select a location of a portion of a lens of the eye to be measured; and
    an optical unit coupled to a processor configured to execute fluorescent ligand scanning on the selected location of the lens of the eye and to collect data associated with fluorescent ligand scanning performed, wherein the processor displays the data on the display screen for review by the operator;
    the processor being further configured to analyze intensities of light in the image to determine a location of a reference point corresponding to an interface of the eye, the selected location of the portion of the lens of the eye to be measured being selected relative to the reference point, wherein the interface of the eye is along an axis going depthwise into the eye, and wherein the reference point is a member of the group consisting of: an interface of a lens capsule of the eye; an interface between the lens capsule and an anterior chamber of the eye; a posterior lens capsule interface; an air-cornea interface; a cornea-aqueous interface, and an interface of a retina of the eye; and
    the processor being still further configured to perform fluorescent ligand scanning by analyzing intensity of light emitted from the portion of the lens of the eye to determine a physical property of a material or object at the selected location based on fluorescence.

2. The system of claim 1, wherein the data is collected in cycles of no more than 60 msec.

3. The system of claim 2, wherein the system executes up to ten consecutive cycles.

4. The system of claim 1, wherein the data is displayed on the display screen as at least one of: test settings, front view and cross-sectional view images of the eye, and average intensity values for fluorescent ligand scanning.

5. The system of claim 1, wherein the data collected includes average fluorescence intensity associated with fluorescent ligand scanning performed.

6. The system of claim 5, wherein a ratio ($FLS_{Norm}$) between the average fluorescence intensity ($I_{FLS-N}$) associated with fluorescent ligand scanning of a location in the nucleus region of the lens of the eye and average fluorescence intensity ($I_{FLS-SN}$) associated with fluorescent ligand scanning of a location in the supranucleus region of the lens of the eye is determined in accordance with the equation $FLS_{Norm}=I_{FLS-SN}/I_{FLS-N}$, where an increase in $FLS_{Norm}$ indicates an increase in the presence of the material or object in the eye.

7. The system of claim 1, wherein the data is collected from at least one of a nucleus region of the lens of the eye and a supranucleus region of the lens of the eye.

8. The system of claim 1, wherein the material or object is β-amyloid protein.

9. The system of claim 1, wherein at least a portion of the data collected is used to track the progress of a disease.

10. The system of claim 1, wherein the measurement quality of fluorescent ligand scanning is analyzed using curve $y(t)=Ie^{-kt}$, where I is the average intensity, k is the decay time constant and t is time.

11. The system of claim 1, wherein the processor measures first data of fluorescence of the eye before introducing an imaging agent into the eye and measures second data of fluorescence of the eye after introducing the imaging agent, and compares the first data with the second data.

12. The system of claim 11, wherein comparing the first data with the second data includes subtracting the first data from the second data.

13. The system of claim 1, wherein the physical property of material comprises a presence of aggregates in a supranucleus of the eye.

14. A method of performing fluorescent ligand scanning to a subject's eye, the method comprising:
    analyzing intensities of light in an image of the eye to determine a location of a reference point corresponding to an interface of the eye, wherein the interface of the eye is along an axis going depthwise into the eye, and wherein the reference point is a member of the group consisting of: an interface of a lens capsule of the eye; an interface between the lens capsule and an anterior chamber of the eye; a posterior lens capsule interface; an air-cornea interface; a cornea-aqueous interface, and an interface of a retina of the eye;
    selecting a location, relative to the reference point, of a portion of a lens of the subject's eye to be analyzed;
    performing fluorescent ligand scanning on the selected location by analyzing intensity of light emitted from the portion of the lens of the subject's eye to determine a physical property of a material or object at the selected location based on fluorescence;
    collecting data associated with the fluorescent ligand scanning so performed; and
    presenting the data for operator review.

15. The method of claim 14, wherein the data collected includes average fluorescence intensity associated with fluorescent ligand scanning performed.

16. The method of claim 15, wherein the average intensity data is collected from locations in a nucleus region of the lens of the eye and a supranucleus region of the lens of the eye and a ratio between the average fluorescence intensity from the nucleus region of the lens of the eye and average fluorescence intensity from the supranucleus region of the lens of the eye is determined.

17. The method of claim 14, wherein performing fluorescent ligand scanning comprises: illuminating the subject's eye; measuring first data of fluorescence of the eye before introducing an imaging agent into the eye; introducing the imaging agent into the eye; measuring second data of fluorescence of the eye after introducing the imaging agent into the eye; and comparing the first data with the second data.

18. The method of claim 17, wherein comparing the first data with the second data includes subtracting the first data from the second data.

19. The method of claim 17, wherein the data is the average fluorescence intensity from the eye.

20. The method of claim 17, wherein the measurement of the second data is taken no more than 24 hours after introducing the imaging agent into the eye.

21. The method of claim 14, wherein the material or object is β-amyloid.

22. The method of claim 14, wherein the progress of a disease can be tracked by measuring levels of fluorescence in the eye.

23. A system for performing fluorescent ligand scanning on a subject's eye, the system comprising:
- a light source configured to transmit light toward the subject's eye;
- a lens configured to focus light sent from the source and received from the subject's eye;
- a measurement reflector disposed to receive at least a portion of the focused light and configured to reflect a first portion of the received light;
- a camera configured and disposed to receive at least a portion of the received light and configured to provide indicia of an image corresponding to the first portion of the received light;
- a display screen for displaying the image to allow an operator to select, relative to a reference point corresponding to an interface of the eye, a location of a portion of a lens of the subject's eye for analyzing; and
- a processor coupled to the camera and configured to analyze intensities of light in the image to determine a location of the reference point corresponding to the interface of the eye, wherein the interface of the eye is along an axis going depth wise into the eye, and wherein the reference point is a member of the group consisting of: an interface of a lens capsule of the eye; an interface between the lens capsule and an anterior chamber of the eye; a posterior lens capsule interface; an air-cornea interface; a cornea-aqueous interface, and an interface of a retina of the eye;

the processor being further configured to perform fluorescent ligand scanning by analyzing intensity of light emitted from the portion of the lens of the subject's eye to determine a physical property of a material or object at the selected location based on fluorescence.

24. The system of claim 23, wherein the material or object of interest is β-amyloid.

25. The system of claim 23, wherein average intensity of fluorescence is analyzed for a supranucleus region of the lens of the eye and a nucleus region of the lens of the eye.

26. The system of claim 25, wherein comparing the average fluorescence intensity from the nucleus region of the lens of the eye to the average fluorescence intensity for the supranucleus region of the lens of the eye provides a correlation factor for evaluating the presence of the material or object of interest in the eye.

27. The system of claim 23, wherein the processor measures the fluorescence intensity from a region of the eye before introduction of an imaging agent and after introduction of an imaging agent to determine the difference between the two intensities.

28. The system of claim 23, wherein the processor displays data on the display screen for operator review, the data including information on fluorescent ligand scanning performed, including average intensity of fluorescence.

29. The system of claim 23, further comprising a computer containing computer-readable, computer-executable instructions for controlling the system to execute fluorescent ligand scanning and display data from fluorescent ligand scanning on the display screen.

30. The system of claim 23, wherein the processor evaluates whether data has been effected by movement of the subject while fluorescent ligand scanning is being performed.

* * * * *